US011028409B2

(12) United States Patent
Neubert et al.

(10) Patent No.: US 11,028,409 B2
(45) Date of Patent: Jun. 8, 2021

(54) REPLICATION-DEFICIENT RNA VIRUSES AS VACCINES

(71) Applicant: MAX-PLANK GESELLSCHAFT ZUR FORDERUNG DER WISSENSCHAFTEN E.V., Munich (DE)

(72) Inventors: Wolfgang J. Neubert, Greifenberg (DE); Sascha Bossow, Augsburg (DE); Sabine Schlecht, Munich (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 0 days.

(21) Appl. No.: 15/605,568

(22) Filed: May 25, 2017

(65) Prior Publication Data

US 2018/0142256 A1 May 24, 2018

Related U.S. Application Data

(63) Continuation of application No. 11/836,322, filed on Aug. 9, 2007, now abandoned, which is a continuation of application No. PCT/EP2006/001251, filed on Feb. 10, 2006.

(30) Foreign Application Priority Data

Feb. 11, 2005 (DE) ........................ 102005006388.8

(51) Int. Cl.

| | |
|---|---|
| ***C12N 15/63*** | (2006.01) |
| ***C12N 15/86*** | (2006.01) |
| ***A61K 48/00*** | (2006.01) |
| ***A61K 39/155*** | (2006.01) |

(52) U.S. Cl.

CPC .............. *C12N 15/86* (2013.01); *A61K 48/00* (2013.01); *C12N 15/63* (2013.01); *C12N 2510/00* (2013.01); *C12N 2760/18811* (2013.01); *C12N 2770/36143* (2013.01)

(58) Field of Classification Search

CPC .... C12N 15/63; C12N 15/86; C12N 2510/00; C12N 2760/18811; C12N 2770/36143

USPC ................. 435/320.1, 455; 424/93.21, 211.1

See application file for complete search history.

(56) References Cited

U.S. PATENT DOCUMENTS

| | | | |
|---|---|---|---|
| 7,442,544 | B2 | 10/2008 | Nagai et al. |
| 2005/0130123 | A1 | 6/2005 | Inoue et al. |

FOREIGN PATENT DOCUMENTS

| | | | |
|---|---|---|---|
| EP | 702085 A1 | 3/1996 | |
| EP | 863202 A1 | 9/1998 | |
| EP | 1437593 A1 | 7/2004 | |
| WO | 2001042445 A2 | 6/2001 | |
| WO | 2003025570 A1 | 3/2003 | |
| WO | 2004113517 A2 | 12/2004 | |
| WO | 2006084746 A1 | 8/2006 | |

OTHER PUBLICATIONS

Pandey, Prativa, 2007, Abstracts, 59th Southeast regional Meeting of the American Chemical Society, Greenville, SC, United States, GEN-671, Publisher: American Chemical Society, Washington D.C.*
Bryan et al., 2013, http://www.elsevierblogs.com/currentcomments/?p=962, Implications of protein fold switching, p. 1-4.*
Maqbool et al., 2015, Biochemical Society Transactions, vol. 43, No. 5, p. 1011-1017.*
Bitzer et al., Negative-Strand RNA Viral Vectors: Intravenous Application of Sendai Virus Vectors for the Systemic Delivery of Therapeutic Genes, (Mol. Therapy 7 (2003), 210-217).
Buchholz et al., Generation of Bovine Respiratory Syncytial Virus (BRSV) from cDNA: BRSV NS2 Is Not Essential for Virus Replication in Tissue Culture, and the Human RSV Leader Region Acts as a Functional BRSV Genome Promoter, (1999) J. Virol. 73, 251-259.
Bukreyev et al., Recovery of Infectious Respiratory Syncytial Virus Expressing an Additional, Foreign Gene, (J. Viral. 70 (1996), 6634-6641).
Chattopadhyay et al., 2004, Virus Research, vol. 99, p. 139-145.
Cortese, Mutations in Domain V of the Sendai Virus L Polymerase Protein Uncouple Transcription and Replication and Differentially Affect Replication In Vitro and in Vivo, Virology 277, 387-396.
Curran et al., J. Viral. 69 (1995). 849-855.
Curran et al., 1994, Virology, vol. 202, p. 875-884.
Curran, Reexamination of the Sendai Virus P Protein Domains Required for RNA Synthesis: A Possible Supplemental Role for the P Protein, Virology 221, 130-140 (1996).
Curran, Joseph et al., "The Sendai Virus P Gene Expresses Both an Essential Protein and an Inhibitor of RNA Synthesis by Shuffling Modules via mRNA Editing," The EMBMO Journal, vol. 10, pp. 3079-3085, 1991.

(Continued)

*Primary Examiner* — Shin Lin Chen
(74) *Attorney, Agent, or Firm* — Amin, Turocy & Watson, LLP

(57) ABSTRACT

A genome-replication-deficient and transcription/competent negative/strand RNA virus, which can be used for the expression of transgenes and in particular for the area of vaccine development. In particular, a recombinant Sendia virus containing a viral genome with a mutation in the gene P, which leads to loss of capacity for replication without loss of capacity for secondary transcription, and at least one sequence coding for a heterologous gene product. Furthermore, a nucleocapsid of the Sendai virus, a genome of the Sendai virus, a DNA molecule that codes for the genome and/or antigenome of the Sendai virus. One aspect is a pharmaceutical composition containing the Sendai virus, the nucleocapsid, or the viral genome as active substance, and a medical use thereof, especially as a vaccine.

24 Claims, 12 Drawing Sheets

Specification includes a Sequence Listing.

(56) References Cited

OTHER PUBLICATIONS

Elroy-Stein et al., (1989) PNAS 86, 6126-6130.
Feller et al., 2000, Virology, vol. 276, p. 190-201.
Finke et al., 2004, Journal of Virology, vol. 78, No. 22, p. 12333-12343.
Hasan et al., Creation of an infectious recombinant Sendai virus expressing the firefly luciferase gene from the 3« proximal first locus, (J. Gen. Viral. 78 (1997), 2813-2820.
Kanda et al., 1982, Microbiol. Immunol., vol. 26 (11), p. 1045-1055.
Kaye et al., 1990, Proc. Natl. Acad. Sci. USA, vol. 87, pp. 6922-6926.
Khattar, Deletion and Substitution Analysis Defines Regions and Residues within the Phosphoprotein of Bovine Respiratory Sncytial Virus That Affect Transcription, RNA Replication and Interaction with the Nucleoportein, Virology 285, 253-269.
Kido, Hirsoshi et al.,"Cellular Proteases Involved in the Pathogenicity of Enveloped Animal Viruses, Human Immunodeficiency Virus A and Sendai Virus," Advan. Enzyme Regul., vol. 36, pp. 325-347, 1996.
Lamb et al., Paramyovirdae: The Viruses and their Replication Fields Virology, 4, Ausgabe (2001), Lippincott, Williams & Wilkins, Philadelphia, 1305-1340).
Leyrer et al., Rapid and efficient recovery of Sendai virus from cDNA: factors influencing recombinant virus rescue, J. Virol. Meth. 75 (1998), 47-58.
Masaki et al., Recombinant Sendai virus-mediated gene transfer to vasculature: a new class of efficient gene transfer vector to the vascular system, (FASEBVB J. 15 (2001), 1294-1296).
Myers, An Amino-Terminal Domain of the Sendai Virus Nucleocapsid Protein is Required for Template Function in Viral RNA Synthesis, J. of Virology, Feb. 1997, p. 918-924.
Schmidt et al., J. Viral., Recombinant Bovine/Human Parainfluenza Virus Type 3 (B/HPIV3) Expressing the Respiratory Syncytial Virus (RSV) G and F Proteins Can Be Used to Achieve Simultaneous Mucosal Immunization against RSV and HPIV3, 75(2001), 4594-4603.
Shiotani et al., Skeletal muscle regeneration after insulin-like growth factor I gene transfer by recombinant Sendai virus vector, (Gene Therapy 7 (2001), 1043-1050.
Shoji et al., Generation and characterization of P gene-deficient rabies virus, (Virology 318 (2004), 295-305.
Skolnick et al., 2000, Trends in Biotech, vol. 18, p. 34-39.
Smallwood et al., 2002, Virology, vol. 304, p. 135-145.
Smallwood et al., 2004, Virology, vol. 318, p. 439-450.
Sutter et al., Non-replicating vaccinia vector efficiently expresses bacteriophage T7 RNA polymerase, (1995) FEBS 371, 9-12.
Willenbrink and Neubert, J., Viral. 68 (1994), 8413-8417.
Yu et al., Gene to Cells (1997), 2, 457-466.
Office Action from U.S. Appl. No. 11/836,322 dated Feb. 24, 2010.
Office Action from U.S. Appl. No. 11/836,322 dated Mar. 9, 2011.
Office Action from U.S. Appl. No. 11/836,322 dated Nov. 4, 2011.
Office Action from U.S. Appl. No. 11/836,322 dated May 29, 2012.
Office Action from U.S. Appl. No. 11/836,322 dated Aug. 9, 2013.
Office Action from U.S. Appl. No. 11/836,322 dated Jan. 9, 2014.
Office Action from U.S. Appl. No. 11/836,322 dated Aug. 27, 2015.
Office Action from U.S. Appl. No. 11/836,322 dated Apr. 13, 2016.
Office Action from U.S. Appl. No. 11/836,322 dated Nov. 28, 2016.

* cited by examiner

SEQUENCE LISTING

<160> NUMBER OF SEQ ID NOS: 28

<210> SEQ ID NO 1
<211> LENGTH: 19
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 1
ggaaacagct atgaccatg 19

<210> SEQ ID NO 2
<211> LENGTH: 58
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 2
ggatcattag taccttgaag cctcgtagat cgcggccgcg tgaactttgg cagcaaag 58

<210> SEQ ID NO 3
<211> LENGTH: 57
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 3
ggcttcaagg tactaatgat ccgtagtaag aaaaacttag ggtgaaagta ttccacc 57

<210> SEQ ID NO 4
<211> LENGTH: 18
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 4
ggtaggtgtc tatgaggc 18

<210> SEQ ID NO 5
<211> LENGTH: 44
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 5
ggaaggaaaa gcggccgccg gcgggatcat acgaggcttc aagg 44

<210> SEQ ID NO 6
<211> LENGTH: 57
<212> TYPE: DNA
<213> ORGANISM: artificial
<220> FEATURE:
<223> OTHER INFORMATION: oligonucleotide

<400> SEQUENCE: 6
cctgtgtttc tgcggccgcc gttcgcgagg ccggcccgtg aactttggca gcaaagc 57

<210> SEQ ID NO 7
<211> LENGTH: 44
<212> TYPE: DNA
<213> ORGANISM: artificial
<220> FEATURE:
<223> OTHER INFORMATION: artificial sequence

<400> SEQUENCE: 7
cgcgggcccg gggcggccgc gtcgccacca tggtgagcaa gggc 44

<210> SEQ ID NO 8
<211> LENGTH: 26
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 8
gatgcatgct cgagcggccg ctttac 26

<210> SEQ ID NO 9
<211> LENGTH: 36
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 9
ggattactat cgccggcggt cgccaccatg gtgagc 36

<210> SEQ ID NO 10
<211> LENGTH: 38
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 10
cgctaactgt cgccggcgtt tacttgtaca gctcgtcc 38

<210> SEQ ID NO 11
<211> LENGTH: 36
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 11
cggatcaagt ggccggccgt cgccaccatg gtgcgc 36

<210> SEQ ID NO 12
<211> LENGTH: 42
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 12
cgcgaatatc ggccggccaa gtctacagga acaggtggtg gc 42

<210> SEQ ID NO 13
<211> LENGTH: 19
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 13
ggaaacagct atgaccatg 19

<210> SEQ ID NO 14
<211> LENGTH: 36
<212> TYPE: DNA
<213> ORGANISM: artificial
<220> FEATURE:

-continued

<223> OTHER INFORMATION: artificial sequence
<220> FEATURE:
<223> OTHER INFORMATION: oligonucleotide

<400> SEQUENCE: 14
cggtgcgggc ccgcacgtga actttggcag caaagc 36

<210> SEQ ID NO 15
<211> LENGTH: 28
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 15
gttcacgtgc gggcccgatc atacgagg 28

<210> SEQ ID NO 16
<211> LENGTH: 19
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 16
cgcgtctcgg gatgattcg 19

<210> SEQ ID NO 17
<211> LENGTH: 17
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 17
ccctgacaca ctccttc 17

<210> SEQ ID NO 18
<211> LENGTH: 31
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 18
gcgccgctcg aggcggtaag tgtagccgaa g 31

<210> SEQ ID NO 19
<211> LENGTH: 34
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 19
cctgcgctcg agctcatccc gggtgaggca tccc 34

-continued

<210> SEQ ID NO 20
<211> LENGTH: 30
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 20
ggcgacgcgt cagtctcaca gcctaattcg 30

<210> SEQ ID NO 21
<211> LENGTH: 47
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 21
cccccttttt ctcgagatgt cgacccaaga taatcgatca ggtgagg 47

<210> SEQ ID NO 22
<211> LENGTH: 46
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 22
tttttccccc ctcgagttac tagttggtca gtgactctat gtcctc 46

<210> SEQ ID NO 23
<211> LENGTH: 20
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 23
agcatatatc cagaggtcac 20

<210> SEQ ID NO 24
<211> LENGTH: 24
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 24
gggactaatt agtcgggccc gacc 24

<210> SEQ ID NO 25
<211> LENGTH: 28
<212> TYPE: DNA
<213> ORGANISM: artificial
<220> FEATURE:
<223> OTHER INFORMATION: artificial sequence
<220> FEATURE:
<223> OTHER INFORMATION: oligonucleotide -continued

<400> SEQUENCE: 25
gcacttgggc ccgactaatt agtccctc 28

<210> SEQ ID NO 26
<211> LENGTH: 21
<212> TYPE: DNA
<213> ORGANISM: artificial
<220> FEATURE:
<223> OTHER INFORMATION: artificial sequence
<220> FEATURE:
<223> OTHER INFORMATION: oligonucleotide

<400> SEQUENCE: 26
cgaatggcgc gcctgatgcg g 21

<210> SEQ ID NO 27
<211> LENGTH: 558
<212> TYPE: PRT
<213> ORGANISM: artificial
<220> FEATURE:
<223> OTHER INFORMATION: artificial sequence
<220> FEATURE:
<223> OTHER INFORMATION: chimeric protein

<400> SEQUENCE: 27

```
Met Pro Thr Ser Ile Leu Leu Ile Ile Thr Thr Met Ile Met Ala Ser
1               5                   10                  15

Phe Cys Gln Ile Asp Ile Thr Lys Leu Gln His Val Gly Val Leu Val
            20                  25                  30

Asn Ser Pro Lys Gly Met Lys Ile Ser Gln Asn Phe Glu Thr Arg Tyr
        35                  40                  45

Leu Ile Leu Ser Leu Ile Pro Lys Ile Glu Asp Ser Asn Ser Cys Gly
    50                  55                  60

Asp Gln Gln Ile Lys Gln Tyr Lys Arg Leu Leu Asp Arg Leu Ile Ile
65                  70                  75                  80

Pro Leu Tyr Asp Gly Leu Arg Leu Gln Lys Asp Val Ile Val Ser Asn
                85                  90                  95

Gln Glu Ser Asn Glu Asn Thr Asp Pro Arg Thr Lys Arg Phe Phe Gly
            100                 105                 110

Gly Val Ile Gly Thr Ile Ala Leu Gly Val Ala Thr Ser Ala Gln Ile
        115                 120                 125

Thr Ala Ala Val Ala Leu Val Glu Ala Lys Gln Ala Arg Ser Asp Ile
    130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Lys Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Ser Leu Gln Glu Lys
    210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
```

-continued

```
            260                 265                 270

Asp Tyr Ser Ile Thr Leu Gln Val Arg Leu Pro Leu Leu Thr Arg Leu
        275                 280                 285

Leu Asn Thr Gln Ile Tyr Arg Val Asp Ser Ile Ser Tyr Asn Ile Gln
    290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Met
            340                 345                 350

Glu Ser Cys Leu Ser Gly Asn Ile Ser Gln Cys Pro Arg Thr Val Val
        355                 360                 365

Lys Ser Asp Ile Val Pro Arg Tyr Ala Phe Val Asn Gly Gly Val Val
    370                 375                 380

Ala Asn Cys Ile Thr Thr Thr Cys Thr Cys Asn Gly Ile Gly Asn Arg
385                 390                 395                 400

Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
            420                 425                 430

Gly Thr Leu Ala Phe Tyr Thr Pro Asn Asp Ile Thr Leu Asn Asn Ser
        435                 440                 445

Val Ala Leu Asp Pro Ile Asp Ile Ser Ile Glu Leu Asn Lys Ala Lys
    450                 455                 460

Ser Asp Leu Glu Glu Ser Lys Glu Trp Ile Arg Arg Ser Asn Gln Lys
465                 470                 475                 480

Leu Asp Ser Ile Gly Asn Trp His Gln Ser Ser Thr Thr Val Ile Thr
                485                 490                 495

Ile Ile Val Val Met Val Val Ile Leu Val Val Ile Ile Val Ile Val
            500                 505                 510

Ile Val Leu Tyr Arg Leu Lys Arg Ser Met Leu Met Gly Asn Pro Asp
        515                 520                 525

Asp Arg Ile Pro Arg Asp Thr Tyr Thr Leu Glu Pro Lys Ile Arg His
    530                 535                 540

Met Tyr Thr Asn Gly Gly Phe Asp Ala Met Ala Glu Lys Arg
545                 550                 555


<210> SEQ ID NO 28
<211> LENGTH: 579
<212> TYPE: PRT
<213> ORGANISM: artificial
<220> FEATURE:
<223> OTHER INFORMATION: artificial sequence
<220> FEATURE:
<223> OTHER INFORMATION: chimeric protein

<400> SEQUENCE: 28

Met Asp Gly Asp Arg Gly Lys Arg Asp Ser Tyr Trp Ser Thr Ser Pro
1               5                   10                  15

Ser Gly Ser Thr Thr Lys Leu Ala Ser Gly Trp Glu Arg Ser Ser Lys
            20                  25                  30

Val Asp Thr Trp Leu Leu Ile Leu Ser Phe Thr Gln Trp Ala Leu Ser
        35                  40                  45

Ile Ala Thr Val Ile Ile Cys Ile Ile Ile Ser Ala Asn Ser Ile Lys
    50                  55                  60
```

-continued

Ser Glu Lys Ala His Glu Ser Leu Leu Gln Asp Val Asn Asn Glu Phe
65 70 75 80

Met Glu Val Thr Glu Lys Ile Gln Met Ala Ser Asp Asn Ile Asn Asp
85 90 95

Leu Ile Gln Ser Gly Val Asn Thr Arg Leu Leu Thr Ile Gln Ser His
100 105 110

Val Gln Asn Tyr Ile Pro Ile Ser Leu Thr Gln Gln Met Ser Asp Leu
115 120 125

Arg Lys Phe Ile Ser Glu Ile Thr Ile Arg Asn Asp Asn Arg Glu Val
130 135 140

Pro Pro Gln Arg Ile Thr His Asp Ala Gly Ile Lys Pro Leu Asn Pro
145 150 155 160

Asp Asp Phe Trp Arg Cys Thr Ser Gly Leu Pro Ser Leu Met Lys Thr
165 170 175

Pro Lys Ile Arg Leu Met Pro Gly Pro Gly Leu Leu Ala Met Pro Thr
180 185 190

Thr Val Asp Gly Cys Val Arg Thr Pro Ser Leu Val Ile Asn Asp Leu
195 200 205

Ile Tyr Ala Tyr Thr Ser Asn Leu Ile Thr Arg Gly Cys Gln Asp Ile
210 215 220

Gly Lys Ser Tyr Gln Val Leu Gln Ile Gly Ile Ile Thr Val Asn Ser
225 230 235 240

Asp Leu Val Pro Asp Leu Asn Pro Arg Ile Ser His Thr Phe Asn Ile
245 250 255

Asn Asp Asn Arg Lys Ser Cys Ser Leu Ala Leu Leu Asn Thr Asp Val
260 265 270

Tyr Gln Leu Cys Ser Thr Pro Lys Val Asp Glu Arg Ser Asp Tyr Ala
275 280 285

Ser Ser Gly Ile Glu Asp Ile Val Leu Asp Ile Val Asn His Asp Gly
290 295 300

Ser Ile Ser Thr Thr Arg Phe Lys Asn Asn Asn Ile Ser Phe Asp Gln
305 310 315 320

Pro Tyr Ala Ala Leu Tyr Pro Ser Val Gly Pro Gly Ile Tyr Tyr Lys
325 330 335

Gly Lys Ile Ile Phe Leu Gly Tyr Gly Gly Leu Glu His Pro Ile Asn
340 345 350

Glu Asn Ala Ile Cys Asn Thr Thr Gly Cys Pro Gly Lys Thr Gln Arg
355 360 365

Asp Cys Asn Gln Ala Ser His Ser Pro Trp Phe Ser Asp Arg Arg Met
370 375 380

Val Asn Ser Ile Ile Val Val Asp Lys Gly Leu Asn Ser Ile Pro Lys
385 390 395 400

Leu Lys Val Trp Thr Ile Ser Met Arg Gln Asn Tyr Trp Gly Ser Glu
405 410 415

Gly Arg Leu Leu Leu Leu Gly Asn Lys Ile Tyr Ile Tyr Thr Arg Ser
420 425 430

Thr Ser Trp His Ser Lys Leu Gln Leu Gly Ile Ile Asp Ile Thr Asp
435 440 445

Tyr Ser Asp Ile Arg Ile Lys Trp Thr Trp His Asn Val Leu Ser Arg
450 455 460

Pro Gly Asn Asn Glu Cys Pro Trp Gly His Ser Cys Pro Asp Gly Cys
465 470 475 480

-continued

```
Ile Thr Gly Val Tyr Thr Asp Ala Tyr Pro Leu Asn Pro Thr Gly Ser
                485                 490                 495

Ile Val Ser Ser Val Ile Leu Asp Ser Gln Lys Ser Arg Val Asn Pro
            500                 505                 510

Val Ile Thr Tyr Ser Thr Ser Thr Glu Arg Val Asn Glu Leu Ala Ile
        515                 520                 525

Arg Asn Lys Thr Leu Ser Ala Gly Tyr Thr Thr Thr Ser Cys Ile Thr
    530                 535                 540

His Tyr Asn Lys Gly Tyr Cys Phe His Ile Val Glu Ile Asn His Lys
545                 550                 555                 560

Ser Leu Asp Thr Phe Gln Pro Met Leu Phe Lys Thr Glu Ile Pro Lys
                565                 570                 575

Ser Cys Ser
```

REPLICATION-DEFICIENT RNA VIRUSES AS VACCINES

RELATED APPLICATIONS

This application is a continuation of U.S. application Ser. No. 11/836,322 filed Aug. 9, 2007, which is a continuation of and claims priority to PCT/EP2006/001251 filed Feb. 10, 2006, which in turn claims priority to German application 10 2005 006 388.8 filed Feb. 11, 2005, the entire contents of which are hereby incorporated herein by reference as if recited in their entirety.

DESCRIPTION

The present invention relates to a replication-defective and transcription-competent negative-strand RNA virus, which can be used for the expression of transgenes and in particular for the area of vaccine development.

Figure 1:
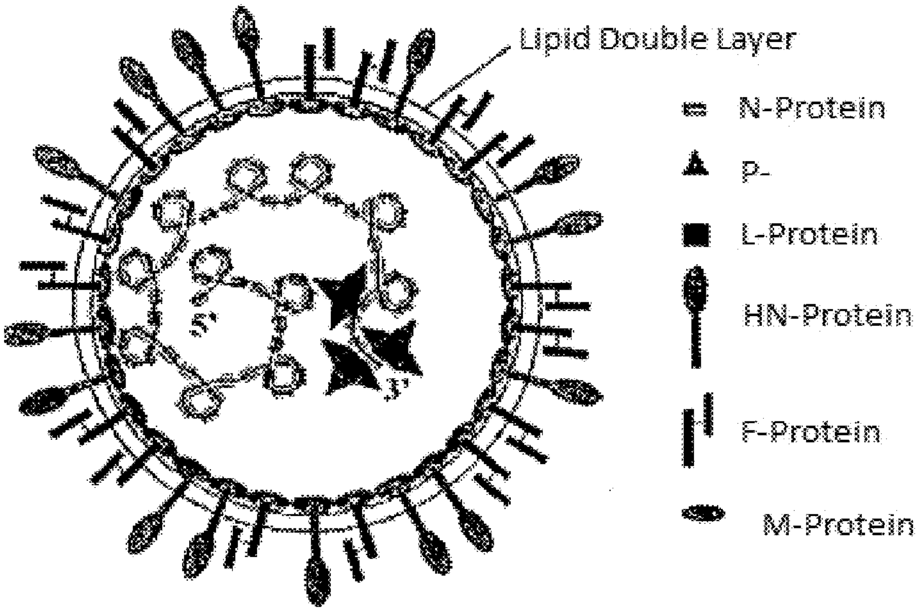
FIG. 1 shows the morphology of a Sendai virus (SeV) according to Fields (Virology. Lippincott, Williams and Wilkins (2001), 4th edition; modified).

Immunizations with live vaccines imitate natural infection and produce a comprehensive immune response. Attenuated, but still viable, viruses are used for vaccination.

Multiplication of the vaccine viruses must take place so slowly that an immunological response and therefore control of multiplication and/or elimination of the virus is ensured. The live vaccine concept has frequently proved itself in various age groups. There are, however, important target groups for whom immunization with live vaccines is problematic and extra safety measures are required: maternal antibodies protect infants in the first few months of life. At the same time they represent a barrier that must be overcome in immunization with live vaccine, though without leading to excessive multiplication of the vaccine virus and associated vaccination lesions. Another target group are the elderly, whose immune system is no longer so efficient, so that it can be overloaded by vaccination, and increased multiplication of the vaccine virus may lead to vaccination lesions. There is therefore the problem of making the immunologically excellent live vaccination even safer for application in certain target groups, as well as increasing the safety profile for general use.

For some years it has been possible to alter negative-strand RNA viruses, such as the rabies virus or the Sendai virus (SeV) for example, purposefully by reverse genetic engineering. EP-A-0 702 085 describes the production of recombinant, infectious, replicating unsegmented negative-strand RNA viruses from cloned cDNA. EP-A-0 863 202 describes a recombinant Sendai virus, in whose genome a heterologous gene is inserted or a gene is deleted or inactivated, but whose genome replication is still intact.

Negative-strand RNA viruses are especially suitable as the backbone of vaccines, as their multiplication in the cytoplasm takes place at the RNA level and genes within the viral genome can simply be exchanged. Thus, there has already been success in producing recombinant viruses with surface proteins of various virus types and using them as vaccines in animal experiments (Schmidt et al., J. Virol. 75 (2001), 45944603 and WO 01/42445). By recombinant insertion of F- and HN-proteins of human parainfluenza virus type 3 (hPIV 3) and of the G- or F-protein of Respiratory Syncytial Virus (RSV) in a vector based on bovine parainfluenza virus type 3 (bPIV 3), a mucosal immune response to hPIV 3 and RSV was detected after application in hamsters. A bivalent antigenicity of this live vaccine, which has been tested in animal experiments, has thus already been achieved.

Owing to the involvement of the species barrier, this bovine parainfluenza virus with human PIV 3 and RSV surface antigens should already be sufficiently attenuated for application in humans. Reversions to the wild type should not be expected, as complete genes were exchanged for viral surface proteins. Clinical testing of the vaccine has already begun.

As the virus mutants described are, however, replication-competent, virus multiplication will undoubtedly occur in the vaccinee, the intensity of which is attenuated by modification of the virus, but is not excluded completely. The intensity of the viremia that is to be expected and therefore the side-effects suffered by the vaccinee then depend on individual factors.

Within the scope of the present invention, an attempt is to be made to substantially reduce the risks of live vaccination, and especially the risks for vaccinees in certain target groups.

One approach is the suppression of viral genome replication after application of the vaccine. As a result, multiplication of the virus and corresponding vaccination lesions will not occur, regardless of the vaccinee's state of immunity. A fundamental difficulty in this approach is that the viral RNA polymerase performs two functions: synthesis of viral mRNA and multiplication of the viral genomes. This coupling must be removed in the new vaccine, as the vaccine must now only be capable of synthesis of viral mRNA.

Another problem is that the recombinant virus must perform efficient synthesis of viral mRNA, if it is to be suitable at all as live vaccine. There are thus two basically contradictory requirements, which mean that considerable difficulties are to be expected in the production of safe, but efficient live vaccines based on negative-strand RNA viruses.

Shoji et al. (Virology 318 (2004), 295-305) describe the production and characterization of a P gene-deficient rabies virus. The virus was produced by means of P-protein-expressing helper cells. Without de novo synthesis of P-protein, the viruses are only capable of primary transcription. The slight viral gene expression is manifested in a very weak signal for N-protein in immunofluorescence and only in very few cells, and convincing proof of this slight viral gene expression will only be provided by PCR analysis. Use of this mutant virus in a challenge test in the mouse model should show protection, but there is no control experiment with transcription-inactive virus and the time interval for the viral challenge is too short. The duration of supposed protection is not being investigated. The use of such mutant viruses for the development of an attenuated rabies vaccine therefore seems not to be very promising.

Within the scope of the investigations that led to the present invention, it was found that in paramyxoviruses, decoupling of the replication and transcription functions can be achieved by partially removing the constituents of polymerase that are essential for the genome replication function. This may involve one of the viral proteins N, P and L, or a special functional domain of such a protein. Surprisingly it was found that by mutations in which the function of the proteins encoded by the viral genes N, L and/or P is not deleted completely, but partially, it is possible to produce replication-defective RNA viruses which possess an adequate transcription function to be suitable for the production of live vaccines.

One object of the present invention is thus a recombinant negative-strand RNA virus, which is replication-deficient and transcription-competent. The virus according to the invention contains a viral genome with a mutation in at least one of the genes N, L and P, with the mutation leading to loss of genome replication without loss of secondary transcription capacity.

The virus according to the invention is a prerequisite for the production of live vaccines, especially for the production of live vaccines with an enhanced safety profile, which is especially suitable for use in high-risk patients with a weak or damaged immune system.

The invention also relates to a nucleocapsid of the recombinant virus, comprising the viral negative-stranded RNA, complexed with the proteins N, L and P plus the negative-stranded RNA of the recombinant virus in isolated form.

The invention also relates to a cDNA, which codes for a negative-strand RNA according to the invention, in particular to a viral RNAA and/or an RNA complementary to it.

The invention further relates to a cell line for multiplication of the recombinant negative-strand RNA virus according to the invention.

The recombinant negative-strand RNA virus according to the invention can be obtained by mutation of a starting virus in at least one of the genes N, L and P. The starting virus can be a natural negative-strand RNA virus, especially from the families Paramyxoviridae or Rhabdoviridae or recombinant variants thereof. Especially preferred representatives are paramyxoviruses, e.g. Sendai virus, human or bovine parainfluenza virus, e.g. human parainfluenza virus (hPIV) type 1, 2, 3, 4a or 4b, Newcastle disease virus, mumps virus, measles virus or humanrespiratory syncytial virus (hRSV) or rhabdoviruses, e.g. vesicular stomatitis virus (VSV). Especially preferably, the virus is a Sendai virus, e.g. of the Fushimi strain (ATCC VR105). Recombinant variants of the aforementioned viruses, as described for example in EP-A-702 085, EP-A-0 863 202 or WO 01/42445, are also covered by the invention.

Further preferred negative-strand RNA viruses are representatives of the Rhabdoviridae, Filoviridae, Bornaviridae, Arenaviridae or Bunyaviridae, e.g. VSV. Like other paramyxoviruses, the Sendai virus is an enveloped virus with a helical nucleocapsid (FIG. 1). The envelope consists of a lipid membrane, which is derived from the plasma membrane of the host cell from which the virus was released. Transmembrane glycoproteins, namely the fusion protein (F) and hemagglutinin-neuramidase (HN), are anchored in the viral envelope. The matrix protein (M) lines the inside of the membrane. The nucleocapsid contained in the envelope consists of single-stranded RNA complexed with nucleoprotein (N), with in each case 6 nucleotides of the RNA bound by one N protein, an RNA-dependent RNA polymerase (L) and the cofactor phosphoprotein (P).

Figure 2:
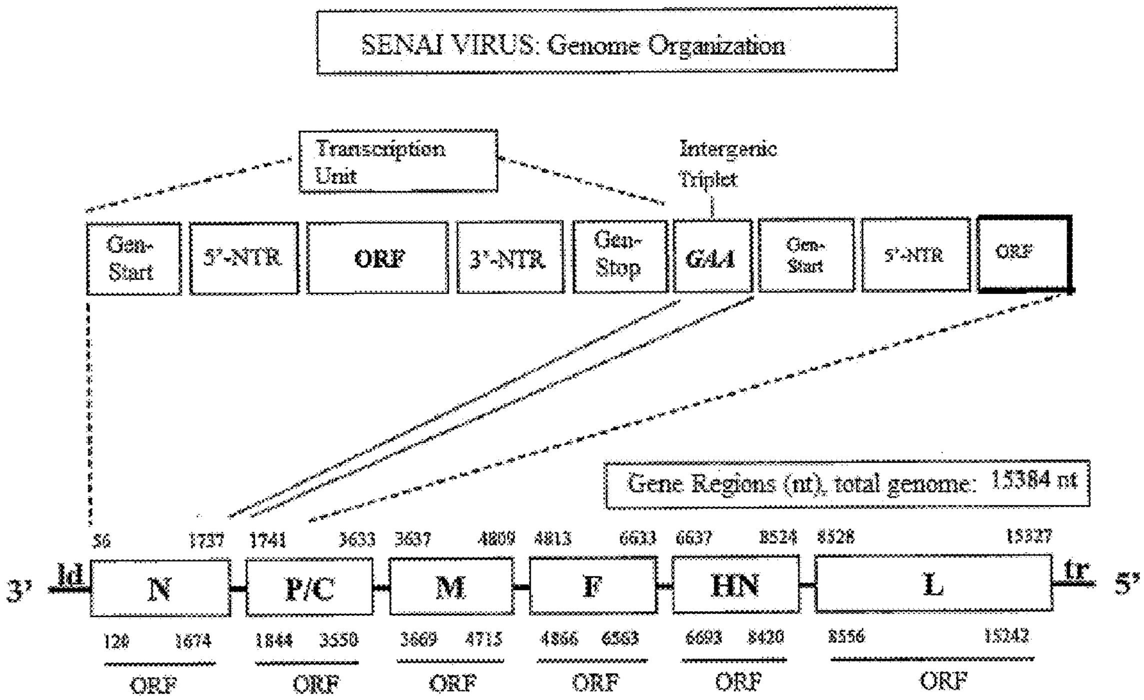
FIG. 2 shows the single-stranded negatively oriented RNA genome of the wild-type Sendai virus which comprises 15384 nucleotides. The genes of the 6 structural proteins are located thereon in the order 3'-N-P/C-M-F-FIN-L-5'.

The negative-strand RNA genome of the Sendai virus contains the genes of the 6 structural proteins in the order: 3'-N-P/C-M-F-HN-L-5' (FIG. 2). The P/C gene codes for a total of 8 proteins, the structural phosphoprotein and all non-structural proteins known to date.

The proteins P, N and L are important for functional transcription and replication (Lamb et al., Paramyxoviridae: The Viruses and their Replication. Fields Virology, 4th edition (2001), Lippincott, Williams & Wilkins, Philadelphia, 1305-1340).

The recombinant negative-strand RNA virus according to the invention contains a mutation in at least one of the genes N, L and P. The mutation can be a deletion, substitution and/or insertion in one of the genes N, L or P, which gives rise to a replication deficiency of the virus, but does not disturb the capacity for transcription. The mutation preferably affects a partial sequence of the proteins encoded by the genes N, L and/or P, which is necessary for replication, whereas other partial sequences necessary for transcription remain functional.

In a preferred embodiment of the invention, the recombinant virus has a mutation in gene P, namely in an N-terminal partial sequence of gene P. The mutation preferably affects at least the region of amino acids 3341 of the protein P, which are important for the capacity for replication. It is further preferred that the C-terminal region (starting from amino acid 320) does not have any mutations impairing the transcription function. Especially preferably, the mutation is a mutation in the region of amino acids 2-77 leading to loss of capacity for replication, for example a deletion of (a) the amino acids 2-77 of the protein encoded by gene P or (b) a partial sequence of (a) sufficient for loss of the capacity for replication. Corresponding mutations can also take place in P proteins of other negative-strand RNA viruses, e.g. of other paramyxoviruses, e.g. hPIV3.

The recombinant virus according to the invention is replication-deficient and transcription-competent. Loss of the capacity for replication means that in a target cell (a cell which does not produce in trans any of the functions deleted by mutation) no detectable virus genome multiplication is found, and in contrast to a reduced or conditional replication deficiency, also no permissive conditions exist, in which replication can occur. The loss of the capacity for replication can be determined as described in Example 8. However, the virus according to the invention is capable of transcribing the gene products encoded by it after infection in a target cell, so that expression of the viral proteins including one or more heterologous gene products can take place in the target cell. It is important that the recombinant virus according to the invention should possess the capacity for secondary transcription, i.e. the viral gene products that arise through primary transcription with the protein components originally contained in the nucleocapsid are capable of bringing about and/or supporting a secondary transcription themselves. The extent of the secondary transcription then leads to protein synthesis of preferably at least 1%, at least 2%, at least 3%, at least 4% or at least 5% relative to a corresponding wild-type virus, i.e. a virus without the mutation in at least one of the genes N, L and P. The capacity for secondary transcription can be reduced relative to the corresponding wild-type virus, though preferably at most by a factor of 20, especially preferably at most by a factor of 10. The capacity for secondary transcription can be determined as in Example 7.1 and/or 7.3 by quantitative determination of the expression of a heterologous gene product, e.g. a reporter protein.

Besides the mutation, the recombinant virus according to the invention preferably contains at least one transgene, i.e. at least one sequence coding for a heterologous gene product. The heterologous gene product can be a protein, for example a reporter protein, e.g. a fluorescence protein such as GFP or a derivative thereof, or an antigen, against which an immune response is to be produced, or a therapeutic protein, e.g. a protein for virotherapy or a functional RNA molecule, e.g. an antisense RNA, a ribozyme or an siRNA molecule capable of RNA interference. Preferably the heterologous gene product is an antigen, originating from a pathogen, such as a virus, a bacterium, a fungus or a protozoon, a tumor antigen or an autoantigen. Especially preferably, the antigen is a viral antigen, derived from a heterologous negative-strand RNA virus, such as a human parainfluenza virus or RSV, e.g. hPIV3 F and HN or hRSV F and G. The virus according to the invention can contain one or more, e.g. two or three, sequences coding for a heterologous gene product.

Sequences coding for heterologous gene products can be inserted in the genome of the recombinant virus. On the other hand, sequences coding for homologous gene products, e.g. genes F and/or HN, can also be substituted with sequences that code for heterologous gene products, e.g. chimeric gene products. Combinations of inserted and substituted transgenes are also possible.

For example, sequences of a Sendai virus can be replaced completely or partially with heterologous sequences of other negative-strand RNA viruses, e.g. with sequences of parainfluenza viruses, e.g. hPIV3, and/or with sequences of RSV. Use of chimeric sequences is especially preferred, i.e. sequences comprising segments of the base virus genome and segments of a heterologous virus genome. For example, chimeric genes F and/or HN can be inserted in the virus genome, which comprise sequences of the base virus genome, e.g. Sendai virus and heterologous sequences, e.g. from human parainfluenza viruses such as hPIV3, and/or RSV.

The recombinant virus can contain one or more different transgenes. If several transgenes are present, these can be of the same or of different origin, which can be derived for example from a single or from several different pathogens, e.g. viruses. Thus, transgenes from several, e.g. 2 or 3 different pathogens, preferably viruses, and especially negative-strand RNA viruses, can be present.

The incorporation of transgenes in paramyxoviruses is described for example in Hasan et al. (J. Gen. Virol. 78 (1997), 2813-2820), Bukreyev et al., (J. Virol. 70 (1996), 6634-6641), Yu et al. (Genes Cells 2 (1997), 457-466), Masaki et al. (FASEBVB J. 15 (2001), 1294-1296), Shiotani et al. (Gene Therapy 8 (2001), 10431050) and Bitzer et al. (Mol. Therapy 7 (2003), 210-217). Preferably the transgenes are inserted in the 3' region of the viral genome. Insertion is effected for example in the form of transcription cassettes, with one or more transcription cassettes with singular restriction sites for integration of the respective reading frames inserted directly after the leader region at the vector level (i.e. at the level of the vector, e.g. of a plasmid vector, which codes for the negative-strand RNA). Integration of several transgenes is preferably effected in independent transcription cassettes in each case. A transcription cassette preferably contains the sequence coding for the heterologous gene product in operational linkage with a transcription start sequence and a transcription termination sequence and preferably translation signals.

A further object of the present invention is a single-stranded or double-stranded DNA molecule, e.g. a cDNA molecule, which codes for a recombinant negative-strand RNA virus genome according to the invention or a precursor thereof or the virus-antigenome or a precursor thereof. The term "precursor" means in this context that the DNA molecule does not yet contain a sequence coding for a heterologous gene product, but only a cloning site for insertion of such a sequence. The cloning site can be a restriction site, for example a singular or non-singular restriction site in the DNA or a multiple cloning site, containing several consecutive restriction sites, preferably singular restriction sites. The DNA molecule coding for the virus genome and/or the complementary sequence is preferably in operational linkage with suitable expression control sequences.

The DNA molecule is preferably a vector, for example a plasmid vector, which is suitable for propagation in a suitable host cell, i.e., in a vector or plasmid amplification cell, preferably in a prokaryotic cell, but also in a eukaryotic cell, especially in a mammalian cell, and has the necessary genetic elements for this, such as replication origin, integration sequences and/or selectable marker sequences.

The DNA molecule contains the sequence coding for the recombinant virus or the complementary sequence, preferably under the control of a transcription signal, so that during transcription with a DNA-dependent RNA polymerase in a host cell suitable for the initial production of the virus, i.e. in a virus production cell, the viral negative-strand RNA can be formed. The transcription signal is selected to permit efficient transcription of the DNA in the host cell used in each case. It is also possible to use a heterologous transcription signal for the particular cell, e.g. a bacteriophage promoter, such as the T7 or SP6 promoter, and then the virus production cell must also contain a corresponding heterologous DNA-dependent RNA polymerase, e.g. T7 or SP6 RNA polymerase, which effects the transcription. In addition to the transcription signal, the DNA molecule further contains, preferably at the 3' end of the sequence coding for the recombinant virus, a transcription terminator and a ribozyme sequence, which permits cleavage of the transcript at the end of the viral sequence. The virus production cell is preferably a eukaryotic cell and especially a mammalian cell.

In addition to the DNA coding for the replication-deficient paramyxovirus, the virus production cell according to the invention also contains helper sequences, whose gene products permit assembly of the recombinant virus RNA according to the invention in trans. For this, the cell can for example additionally contain one or more vectors which produce the N protein, the P protein and/or the L protein in trans. This makes assembly of nucleocapsids of the recombinant virus according to the invention possible in the production cell.

Multiplication of the recombinant virus initially assembled in the virus production cell takes place in a virus multiplication cell, which is infected with the virus according to the invention. In addition the virus multiplication cell contains helper sequences as mentioned above, for production of the N protein and/or the L protein in trans. Preferably a virus multiplication cell is used in which there is stable expression of the helper sequences, e.g. by genomic integration. The virus multiplication cell is preferably a mammalian cell. An especially preferred multiplication cell is cell H29, derived from a 293 cell, of a human embryonic renal fibroblast cell line, or a cell derived from that. Cell H29 was deposited on 11.05.2004 (DSM ACC 2702) in accordance with the provisions of the Budapest Treaty with the Deutsche Sammlung fur Mikroorganismen and Zellkulturen GmbH, Braunschweig, Mascheroder Weg. Vero cells, of a renal cell line from the African green monkey, or cells derived from LLCMK2 cells, of a renal cell line from the rhesus monkey, which have been stably transfected with corresponding helper sequences, e.g. SeV N and P genes, are also suitable.

The invention therefore further relates to a cell, preferably a eukaryotic cell and especially preferably a mammalian cell, which contains (i) a DNA molecule, which codes for the genome of the recombinant virus according to the invention and/or the complementary sequence thereof or a precursor thereof, and/or (ii) an RNA genome of the virus according to the invention. The cell can be a vector multiplication cell, a virus production cell or a virus multiplication cell, as explained previously.

If the cell is a vector multiplication cell, e.g. a plasmid multiplication cell, any cell that is suitable for multiplication of the corresponding vector can be used, e.g. also a prokaryotic cell such as a transformed *E. coli* cell.

If the cell is a virus production or multiplication cell, it contains helper sequences for production of the virus proteins N, P and/or L in trans. The DNA inserted in a virus production cell is preferably under the control of a heterologous transcription signal, and advantageously the cell further contains a DNA that codes for a heterologous DNA-dependent RNA polymerase, which recognizes the heterologous transcription signal and effects transcription of the DNA coding for the recombinant negative-strand RNA virus.

If the cell is a virus multiplication cell, it is infected with a genomic viral RNA molecule, e.g. in the form of a nucleocapsid, and contains the helper sequences in stably expressible form.

The present invention further relates to a method of production of a recombinant negative-strand RNA virus according to the invention comprising the steps: (a) preparation of a virus production cell, which is transfected with a DNA molecule that codes for the genome of a negative-strand RNA virus, containing a mutation in at least one of the genes N, L and P, which leads to loss of the capacity for genome replication without loss of the capacity for transcription, and optionally at least one sequence coding for a heterologous gene product, and (b) cultivation of the host cell in conditions such that transcription of the DNA molecule according to (a) takes place and the recombinant negative-strand RNA virus is formed initially. The host cell is preferably capable of producing the N protein, the P protein and/or the L protein in trans, e.g. by transfection with the corresponding helper plasmids which contain sequences coding for the proteins N, P and/or L.

For the production of large quantities of the nucleocapsids or of the virus particles, preferably a cell is used which stably expresses, constitutively or inducibly, the proteins N, L and/or P, preferably at least protein P of a negative-strand RNA virus. The invention thus also relates to a method of multiplication of a recombinant negative-strand RNA virus according to the invention, comprising the steps: (a) preparation of a virus multiplication cell, which is infected with the genome of a negative-strand RNA virus, containing a mutation in at least one of the genes N, L and P, which leads to loss of the capacity for genome replication without loss of the capacity for transcription, and optionally at least one sequence coding for a heterologous gene product, and (b) cultivation of the host cell in conditions such that multiplication of the virus takes place.

The present invention further relates to a pharmaceutical composition, which contains a recombinant replication-deficient and transcription-competent negative-strand RNA virus, as stated previously, or its nucleocapsid as active substance and optionally as pharmaceutically usual vehicles and/or excipients. The pharmaceutical composition is suitable for applications in human and veterinary medicine. It can be used in particular as vaccine or for antitumor therapy, in particular for application in high-risk patients, such as children, the elderly and/or persons with a damaged or weak immune system. The pharmaceutical composition can contain the negative-strand RNA virus in its native viral envelope.

Application as vaccine is especially preferred, e.g. as vaccine against pathogens such as viruses, bacteria or protozoa. When the recombinant virus contains a transgene or several transgenes of the same origin, e.g. from a single pathogen, it is a monovalent vaccine. When the recombinant virus contains transgenes of various origins, it can be used as a polyvalent vaccine, e.g. as bivalent or trivalent vaccine. For example, it is possible to produce a polyvalent vaccine against several pathogenic viruses, e.g. against several pathogenic negative-strand RNA viruses, such as human parainfluenza virus and RSV.

A vaccine according to the invention is capable of triggering a humoral immune response, preferably the formation of neutralizing antibodies, and/or a T-cell immune response. Especially preferably, a humoral immune response and a T-cell immune response are triggered.

The pharmaceutical composition can be in the form of a solution, a suspension, a lyophilizate or in any other suitable form. In addition to the active substance, the composition can contain agents for adjusting the pH value, buffers, agents for adjusting tonicity, wetting agents and the like, and adjuvants. It can be administered by the usual routes, e.g. oral, topical, nasal, pulmonary etc., in the form of aerosols, liquids, powders etc. The therapeutically effective dose of the virus is administered to the patient, and this dose depends on the particular application (e.g. virotherapy or vaccine), on the type of disease, the patient's weight and state of health, the manner of administration and the formulation etc. Usually $10^3$ to $10^7$ virus particles, especially preferably about $10^4$ to $10^6$ virus particles are administered per application. Optionally, several different virus particles can be administered together, e.g. in the case of combination vaccinations. Administration can be single or multiple, as required.

Preferred fields of application are for example the prevention or treatment of respiratory viral diseases.

The invention will be further explained with the following drawings and examples.

EXAMPLES

1. General

FIG. 1 shows the morphology of a Sendai virus (SeV) according to Fields (Virology. Lippincott, Williams and Wilkins (2001), 4th edition; modified). The genome comprises a single-stranded RNA, which has the proteins N, P and L in the form of a nucleocapsid. The nucleocapsid is surrounded by a membrane envelope, in which the proteins HN and F (each consisting of one $F_1$ and F2 subunit) are incorporated. Protein M is associated with the inside of the membrane, and is also bound to the nucleocapsid components at the same time.

The single-stranded negatively oriented RNA genome of the wild-type Sendai virus comprises 15384 nucleotides. The genes of the 6 structural proteins are located thereon in the order 3'-N-P/C-M-F-HN-L-5' (FIG. 2). Between the genes there are transitions of 50-80 nucleotides, each containing a highly conserved region of 22 nucleotides: the termination signal of the preceding gene, an intergenic sequence and the start signal for the next gene. A unit comprising start signal, open reading frame (ORF), optionally untranslated regions and termination signal is called a transcription cassette. Before the N gene there is a leader sequence (1d) 55 nucleotides long, which is transcribed, but not translated. The L gene is followed by a trailer sequence (tr) 54 nucleotides long. The ld and tr regions function as genomic and antigenomic promoters for the replication of genome or antigenome. With the exception of P/C-RNA, the mRNA molecules formed by transcription are monocistronic.

The multiplication cycle of the Sendai virus comprises entry into the host cell, transcription and translation plus replication and virus maturation followed by release of newly produced viruses. In particular the proteins N, P and L are involved in the transcription process, with L representing the viral RNA-dependent RNA polymerase with all catalytic activities. As the genome of the Sendai virus is in negative-strand orientation, the viral RNA cannot be converted to proteins directly. First there is primary transcription to mRNAs by RNA polymerase, which is brought into the cell associated with the nucleocapsid.

Figure 3:
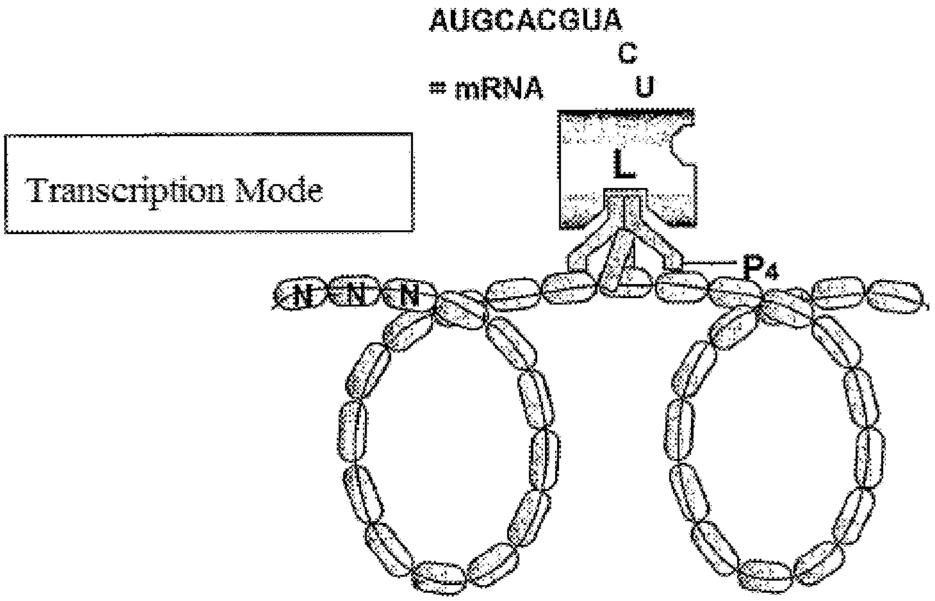
FIG. 3 shows a schematic representation of the transcription mode of the Sendai virus.

FIG. 3 is a schematic representation of the transcription mode of the Sendai virus. The polymerase complex, comprising an L protein and a homotetramer of P proteins, migrates along the RNA packed with N proteins toward the 5' end. The genetic information on the genomic negative-strand RNA is read off and transcribed into positive-strand mRNA.

Figure 4:
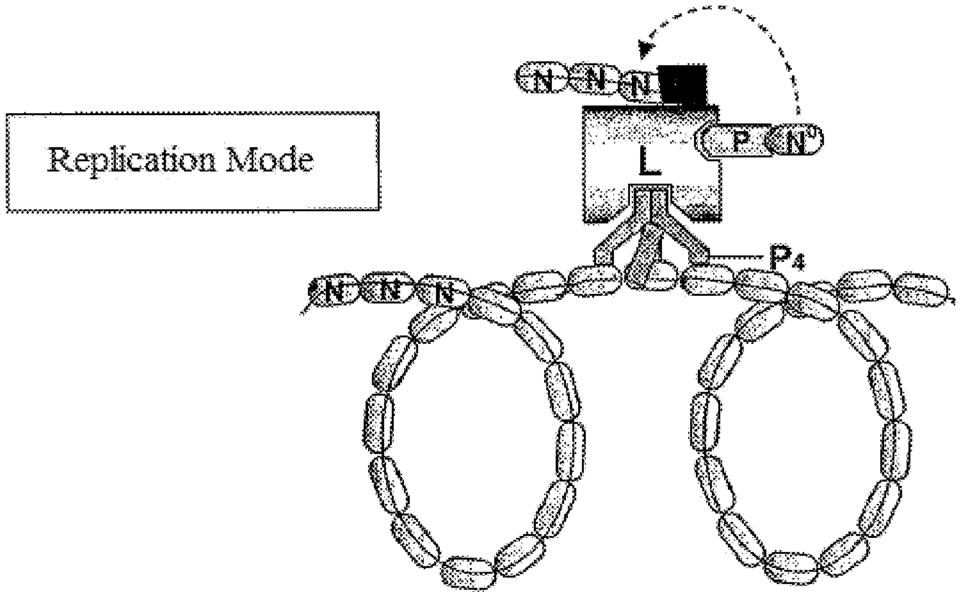
FIG. 4 shows a schematic representation of the replication mode of the Sendai virus.

Replication of the genome comprises the production of new virus genomes with negative polarity. For this, first antigenomes are formed, which then serve as matrixes for the formation of the genomes. As transcription begins at the 3' end of the genome (1d), switching from transcription to replication mode is required. This switching is determined by the amount of free N protein in the cell. Replication cannot take place until sufficient N protein has been formed after translation of mRNA molecules. Once an antigenome, which is complexed with N proteins over its entire length, is present, this can serve as a matrix for the production of further genomes. These are also packed directly with N proteins. Once again the proteins N, P and L are responsible for the process of replication (FIG. 4).

During virus replication, owing to the increasing number of mRNA molecules there is also increasing synthesis of viral proteins. Then complexes of viral RNA and viral proteins (nucleocapsids) are transported in the form of secretory vesicles to the cytoplasmic membrane, where enveloping with viral surface proteins and budding of virus particles occur.

Within the scope of the present invention, recombinant virus mutants are prepared, in which the functions of transcription and replication are decoupled, i.e. the viruses are transcription-competent, but replication-deficient. The missing genome replication function must, for the production of virus particles and/or their nucleocapsids, be compensated by helper cells which complement the missing or functionally deficient viral protein in trans. A preferred helper cell of this kind is the cell line H29 (Willenbrink and Neubert, J. Virol. 68 (1994), 8413-8417). Within the scope of the present application, this cell line was deposited under reference DSM ACC2702 on Nov. 5, 2004 in accordance with the provisions of the Budapest Treaty. For the production of replication-deficient, but transcription-competent viruses, the gene coding for the P protein was not removed completely, but only a domain essential for genome replication. Thus, it was known from earlier works (Curran, Virology 221 (1996), 130-140; Curran et al., J. Virol. 69 (1995), 849-855) that in an in vitro system, on deleting the amino acids 2-77 of protein P, genome replication is inhibited, whereas viral transcription remains active.

Figure 5:
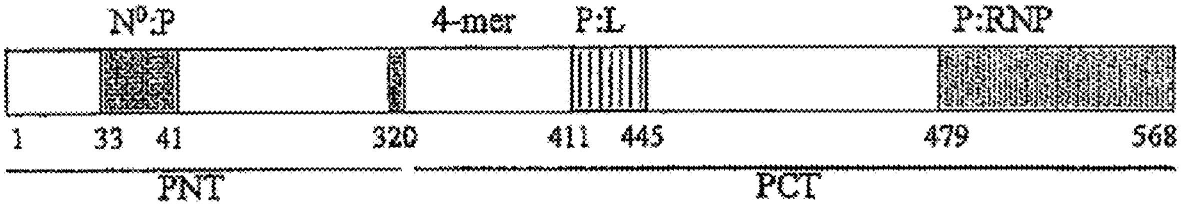
FIG. 5 is a schematic representation of the P protein with its N-terminal and C-terminal domains (PNT, PCT), the tetramerization domain (amino acids 320-446), the P:L domain (amino acids 411-445) and the P:RNP binding domain (amino acids 479-568).

FIG. 5 is a schematic representation of the P protein with its N-terminal and C-terminal domains (PNT, PCT), the tetramerization domain (amino acids 320-446), the P:L domain (amino acids 411-445) and the P:RNP binding domain (amino acids 479-568). For switching off the viral genome replication function while simultaneously retaining the capacity for viral mRNA synthesis, a deletion of the first 77 amino acids of the protein P was selected. Firstly a corresponding Sendai virus mutant (SeV-PΔ2-77) was produced, in which the 5'-terminal region of the P-ORF was deleted. Only N-terminal-shortened P proteins can be encoded by these viruses. Infection studies showed that the virus mutant is not capable of multiplying in cell culture. By means of helper cell line H29 (DSM ACC2702), which among other things provides the required wild-type P protein, multiplication of the virus mutant can be achieved. The efficiency of virus multiplication is approx. 45% compared with wild-type Sendai viruses.

After infection, the virus mutant according to the invention is able to express virus-encoded transgenes in infected cells. The shortened protein P produced by the virus mutant gives sufficient support for secondary viral mRNA synthesis. Synthesis of virus-encoded proteins continues over several days in the infected cells and is only reduced by a factor of approx. 10 relative to the wild-type virus, so that a sufficient immune response can reliably be expected on using the mutant as vaccine.

2. Production of Basic Constructs for Replication-Deficient Sendai Virus Vectors (SeVV)

2.1 Production of a cDNA Construct pSeV-X

An encoding transcription cassette was inserted in the 3' region of SeV, Fushimi strain (ATCC VR105). In all manipulations of the genome it is essential to ensure that the total number of nucleotides of the recombinant SeV genome is divisible by six ("rule of six").

Figure 6:
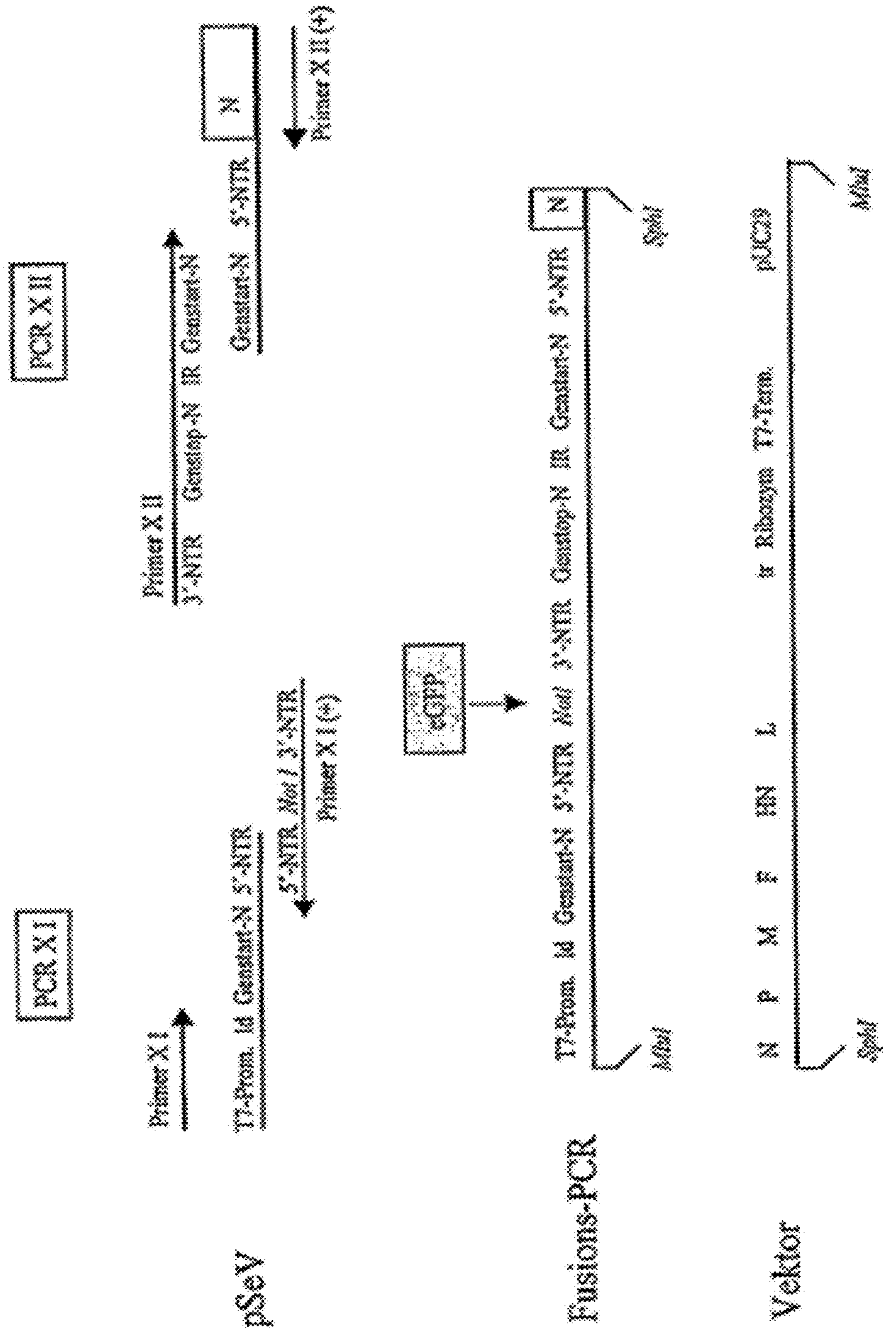
FIG. 6 shows two PCR fragments PCR X I and PCR X II were prepared for the production of pSeV-X, starting from the cDNA pSeV.

Starting from the cDNA pSeV used as matrix, two PCR fragments PCR X I and PCR X II were prepared for the production of pSeV-X (FIG. 6).

PCR X I (370 bp) comprises the sequence of the T7 promoter (T7-prom.), the leader (1d) sequence, the N-gene start with 5'-NTR up to before the start codon of the N-ORF (open reading frame). Via the reverse primer X I (+) (Table 3), a singular Notl restriction site and 24 nucleotides of the N-gene stop sequence were attached. The 24 nucleotides of the N-gene stop sequence of PCR X I, inserted by the mutagenic primer X I (+), serve in the subsequent fusion step as the region overlapping PCR X II.

PCR X II (970 bp) comprises the sequence of the N-gene start and the first third of the N-ORF. Via the forward primer X II, the sequence of the 3'-NTR N and the gene-stop sequence of N, as well as the intergenic region (IR) were attached. The reverse primer XII (+) binds in the first third of the N-ORF just behind the singular Sphl site in the SeV genome. The amplicon PCR X I was complementary, in the 3' region, to the 5' region of PCR X II. Through this overlapping region, the two PCR fragments X I and X II could be fused. After completion of PCR, the fusion product (1310 bp) could be inserted, by restriction cleavage with the enzymes MluI and Sphl, in the vector pSeV, also treated with MluI and Sphl. From the clones obtained, plasmid-DNA was isolated by plasmid preparation, and verified by restriction analysis and sequencing for correct insertion of the transcription cassette. The cDNA construct pSeV-X was thus made available.

So that the production of recombinant viruses can be monitored easily, the gene for the enhanced green fluorescent protein (eGFP) was now inserted in the empty cassette of pSeV-X. The eGFP-ORF was amplified by PCR from the expression plasmid pEGFP-N1 (from Clontech), maintaining the "rule of six" and achieving attachment of two flanking Notl sites by means of mutagenic primers. The resultant 771-bp PCR fragment was cleaved with the restriction enzyme Notl and a 738-bp fragment was isolated by gel elution, and was inserted via the NotI site of pSeV-X in its "empty" transcription cassette pSeV-X. After transformation of *E. coil,* plasmid preparation and subsequent sequencing of the eGFP reading frame inserted via PCR, the cDNA construct pSeV-eGFP was made available.

2.2 Production of the cDNA Construct pSeV-X-X

Figure 7:
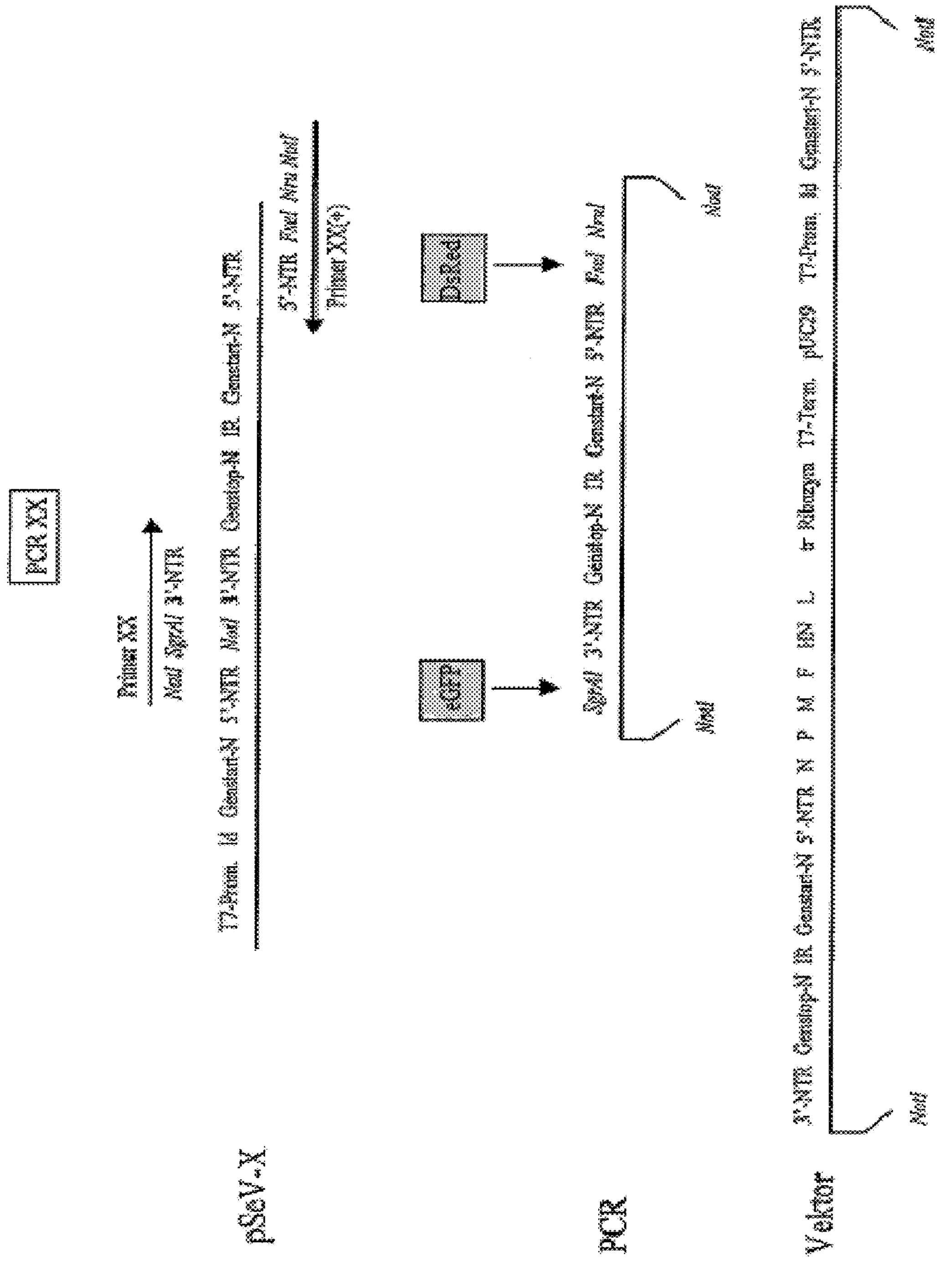
FIG. 7 shows that pSEV-X-X was produced via a PCR reaction, in which pSEV-X served as a template.

With the construct pSeV-X-X, two additional transcription cassettes were to be made available, in which two transgenes can be incorporated. The use of pSeV-X-X as base vector for the production of the replication-deficient vectors should make it possible to equip the vector with multivalent, e.g. trivalent, properties.

pSeV-X-X was produced via a PCR reaction, in which pSeV-X served as template (FIG. 7). The primer XX-forward hybridizes with pSeV-X in the region of the NotI site and the 3'-NTR of the second transcription cassette that is to be integrated. A singular SgrAI restriction site was introduced by means of the XX-forward primer between the NotI site and the 3'-NTR. It serves as singular restriction site for the later insertion of the ORF of a transgene. Gene stop, intergenic region (IR), gene start and 5'-NTR follow in the PCR product XX. The singular restriction sites Fsel and Nru I were inserted by the primer XX (+), which hybridizes with the 5'-NTR. The Fsel site serves for incorporation of the ORF of a second transgene. The singular Nru I site was cloned-in prospectively, so as to be able to integrate a third transcription cassette if necessary. Primer XX (+) hybridizes in the 3' region with the sequence of the Notl site of pSeV-X. The PCR product XX (220 bp) was treated with the restriction enzyme Notl and a fragment of 144 bp was isolated by gel extraction. This fragment, designed maintaining the "rule of six", could then be incorporated in the plasmid pSeV-X, which was also treated with NotI. After checking for correct orientation of the NotI PCR fragment XX and verification of the sequence, the plasmid pSeV-X-X was ready. Any desired transgenes can be integrated in the singular sites SgrAI and FseI.

For the investigations in this work, the two transcription cassettes (X) of pSeV-X-X were provided with reading frames of two different fluorescent proteins. On the one hand, the reading frame for the fluorescent protein eGFP from the expression plasmid pEGFP-N1 was amplified by PCR while observing the "rule of six", attaching two flanking SgrAI sites by means of mutagenic primers. After restriction cleavage with SgrAI and gel elution, the approx. 738-bp fragment could be incorporated in the first transcription cassette of pSeV-X-X (pSeV-eGFP-X). On the other hand, in the same way the ORF of the fluorescent protein DsRed (from the plasmid "pDsRed", from Clontech) was provided by PCR, observing the "rule of six", with the restriction sites of FseI, the DNA was cleaved, gel-eluted and this fragment (702 bp) was then cloned into the second transcription cassette in the 3' region of pSeV-eGFP-X. The result was the genomic SeV cDNA construct pSeV-eGFP-DsRed.

Figure 8A:
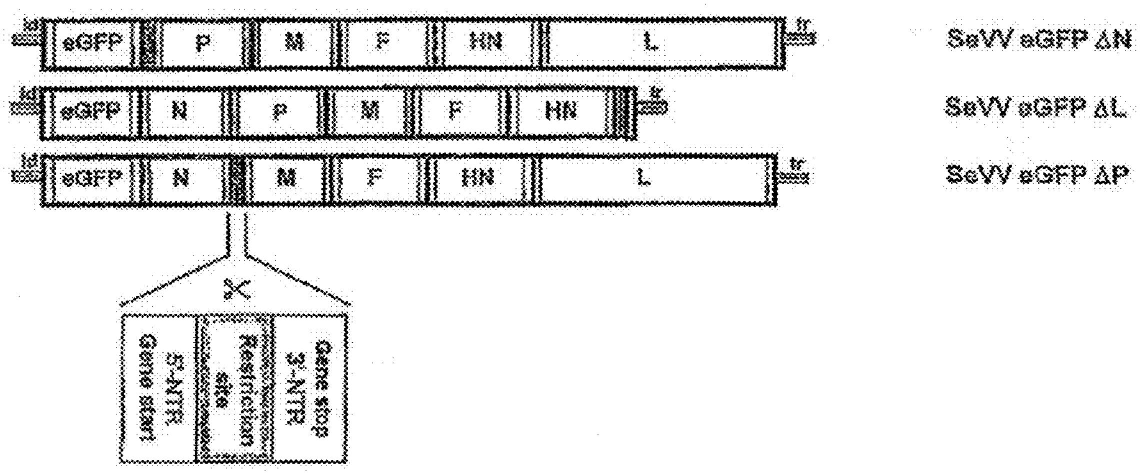
FIG. 8A is an illustration of the production of cDNA constructs.

3. Production of Replication-Deficient Sendai Virus Vectors (SeW)

cDNA constructs pSeVV-eGFP-ON, -LP and -LL were produced, which code for replication-deficient Sendai viruses, in each of which the gene for the protein N, P and L has been deleted. For this, in each case a reading frame of the genes N, P or L had to be deleted while observing the rule of six, and a non-coding transcription cassette was to be retained at the corresponding position (FIG. 8A).

By incorporating a restriction site instead of the deleted ORF, an additional functional transcription cassette, into which a further transgene can be inserted if required, was to be made available, for later applications, in each cDNA construct pSeVV-eGFP-ΔN, -AP and -ΔL.

Figure 8B:
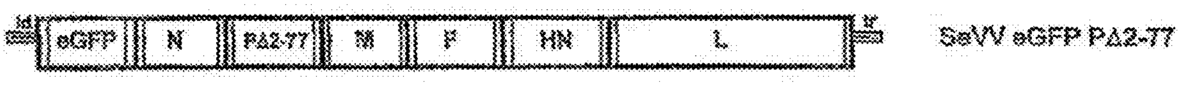
FIG. 8B is an illustration of the production of a replication-deficient SeVV.

As a further variant of a replication-deficient SeVV, the deletion mutant pSeVV-eGFP-PΔ2-77 was produced, which codes for an N-terminal-shortened P protein lacking amino acids 2 to 77 (FIG. 8B).

The clonings pSeVV-eGFP-AN, -ΔP and -ΔL were all carried out according to the same principle. As an example, the cloning of pSeVV-eGFP-ΔP will be described in detail in the next section. Then just the differences in the clonings of pSeVV-eGFP-ΔN, and -LI, will be presented in a table.

3.1 Cloning of the cDNA Constructs pSeVV-eGFP-AP and pSeW-eGFP-PE2-77

The ORF of the P protein was removed from the cDNA construct of the replication-competent virus pSeV-eGFP, to produce the new cDNA pSeVV-eGFP-ΔP, coding for the replication-deficient vector. An Xhol restriction site was used instead of the P-ORF.

For the cloning of pSeVV-eGFP-ΔP, two PCR fragments named PCR ΔP I and PCR ΔP II were produced and then fused. pSeV-eGFP served as template for both PCR reactions. In the case of fragment PCR ΔP I (1272 bp), by means of the forward primer ΔP I(=N-578; Table 3) hybridization with the template in the region of the N ORF was achieved before a singular SiohI site. The reverse primer AP I (+) hybridizes with the template in the 5'-NTR region of the P-gene up to before the ATG codon of P and inserts the restriction site XhoI there.

The fragment PCR ΔP II comprises 1938 bp, and pSeV also serves as template here. The forward primer AP II hybridizes with a portion of the 5'-NTR P sequence and attaches an XhoI site. The reverse primer of PCR ΔP II (+) binds in the ORF of the F gene after a singular Eco47III site and additionally has an artificial MluI site.

Figure 9:
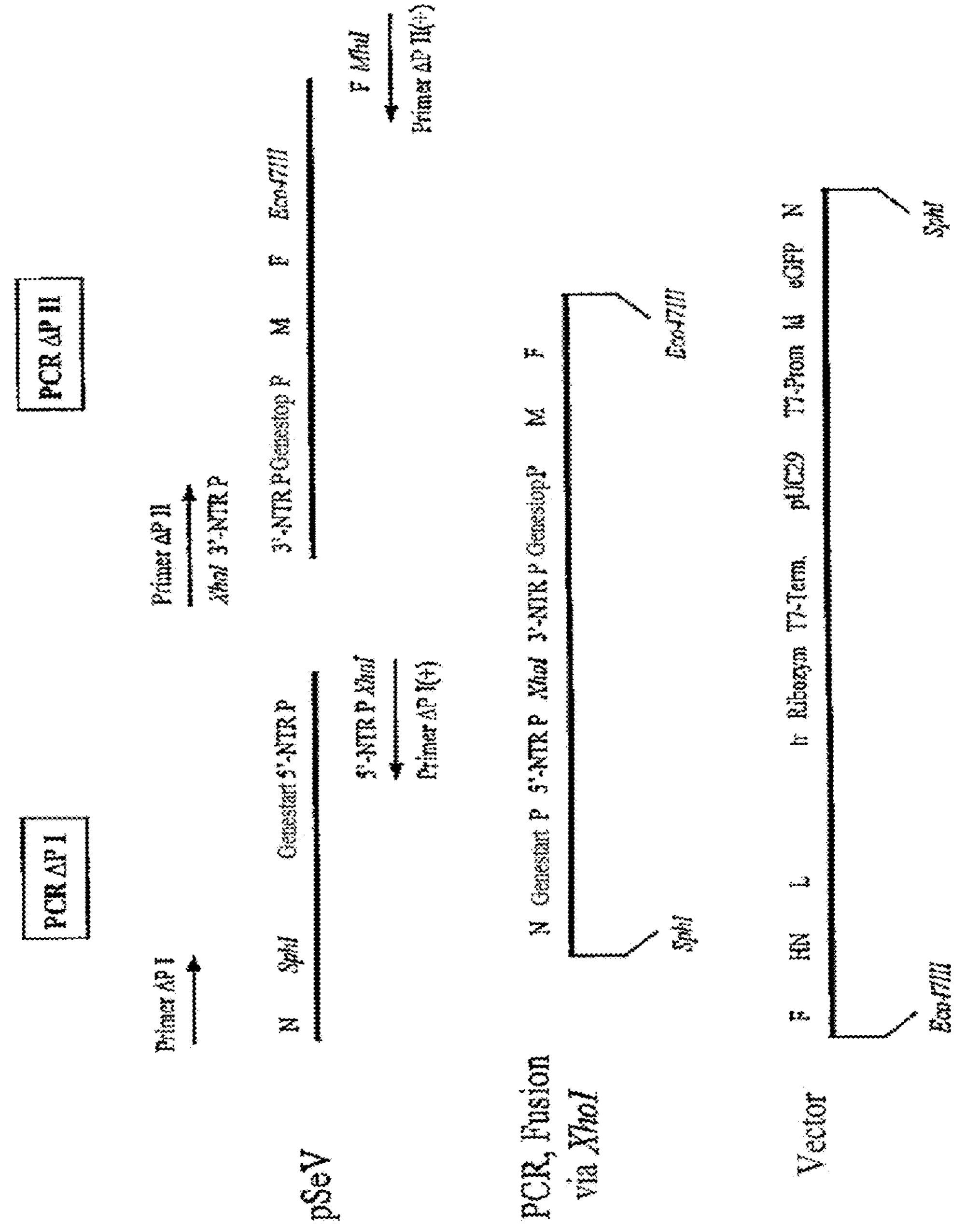
FIG. 9 shows the preparation of a pSeVV-eGFP-ΔP clone (genomic viral cDNA), for the production of the replication-deficient SeVV-eGFP-ΔP.

The two PCR fragments ΔP I and ΔP II were combined via the XhoI site. The fusion product comprising a partial sequence of the N ORF, the non-coding P-transcription cassette with inserted Xhol restriction site, the M plus a quarter of the F ORF—was cleaved with the restriction enzymes Sphl and Miul, intercloned and sequence-verified. An Sphl-Eco47III fragment with a size of 3006 bp was cut out of a subclone with correct sequence and was ligated in the identically treated vector pSeV-eGFP. A corresponding pSeVV-eGFP-ΔP clone (genomic viral cDNA) was now ready, after sequence verification, for the production of the replication-deficient SeVV-eGFP-ΔP (FIG. 9).

A PCR with two mutagenic primers was employed for constructing the deletion mutant pSeVV-eGFP-PΔ2-77. The forward primer "XhoI PΔ2-77" contains an XhoI site, followed by an ATG start codon plus codons for the amino acids 78 to 86 of the P protein. The reverse primer "PΔ2-77 (+) XhoI" contains the last 10 codons of the P protein and an XhoI site. The reading frame of the P protein shortened by 76 amino acids at the N-terminal was produced by PCR, starting from the template pSeV, observing the rule of six. The XhoI-cleaved, 1488-bp fragment was inserted via two cloning steps into the non-coding transcription cassette of pSeVV-eGFP-ΔP at the position of the original P-ORF. After sequence verification, a genomic cDNA clone was now also ready for production of the replication-deficient SeVV-eGFP-PΔ2-77.

Deletion of the codons 2 to 77 in the P ORF has the result that, in the case of the non-structural proteins, the V and W proteins are also shortened at the N-terminal end and, of the C family, only C'—also truncated—is still encoded; because the start codons are missing, the proteins C, Y1 and Y2 can no longer be translated by the shortened mRNA.

3.2. Cloning of the cDNA Constructs pSeVV-eGFP-ΔN and -ΔL

Production of pSeVV-eGFP-ΔN and pSeVV-eGFP-ΔL was carried out by a similar strategy to the cloning of pSeVV-eGFP-ΔP. In order to summarize the cloning procedures, all the decisive parameters are presented in Table 1.

Through the production in each case of two fusible PCR products PCR I and PCR II, the ORF of the genes N or L were removed from pSeV-eGFP, observing the rule of six, and were replaced with a singular Apal restriction site both in pSeVV-eGFP-ΔN and in SeVV-eGFP-ΔL. The sequences of the primers for cloning pSeVV-eGFP-ΔN, -ΔP and -ΔL are listed together with the DNA oligonucleotides used (Table 3). The PCR products obtained, PCR I and PCR II, were fused and amplified using the forward primer of PCR I and the reverse primer of PCR II. Then the fusion PCR products were cleaved with restriction enzymes which occur singly in pSeV-eGFP and allow the insertion of the corresponding fusion product in pSeV-eGFP (e.g.: Nan when cloning pSeVV-eGFP-ΔN, see Table 1). The purified cleavage product was inserted by ligation in the vector pSeV-eGFP, which was also digested with the corresponding enzymes.

TABLE 1

Review of the primers and restriction sites used in the cloning of pSeVV-eGFP-ΔX

| | pSeW-eGFP-ΔN | pSeVV-eGFP-ΔP | pSeVV-eGFP-ΔL |
|---|---|---|---|
| Primer pair PCR I | ΔN I. ΔN I (+) | ΔPI. ΔPI (+) | ΔL I. ΔL I (+) |
| Primer pair PCR II | ΔN II. ΔN II (+) | ΔP II. ΔP II (+) | ΔL II. ΔL II (+) |
| RS[5] of the transcription | Δpal | Xhol | Δ |
| RS[§] of cloning | Narl | Sphl + Eco47III | Eco4711I + Ascl |

[§]RS = restriction sit

*E. coli* cells were transformed with a portion of the ligation preparations and plasmid DNA of the clones obtained was isolated by plasmid mini-preparation. After verification of the correct sequence by restriction analysis and sequencing, a plasmid preparation was prepared from one positive clone in each case (DNA Maxi Prep-Kit, Qiagen), and the various pSeVV-eGFP-ΔX were thus ready for the production of recombinant deletion mutants.

4. Production of Replication-Deficient Virus Mutants

Replication-deficient SeV vectors (SeVV-eGFP-ΔX) were produced in cell culture from the cDNA constructs pSeVV-eGFP-ΔN, -ΔP and -ΔL.

4.1 Initial Production of SeVV-eGFP-ΔX

Figure 10:
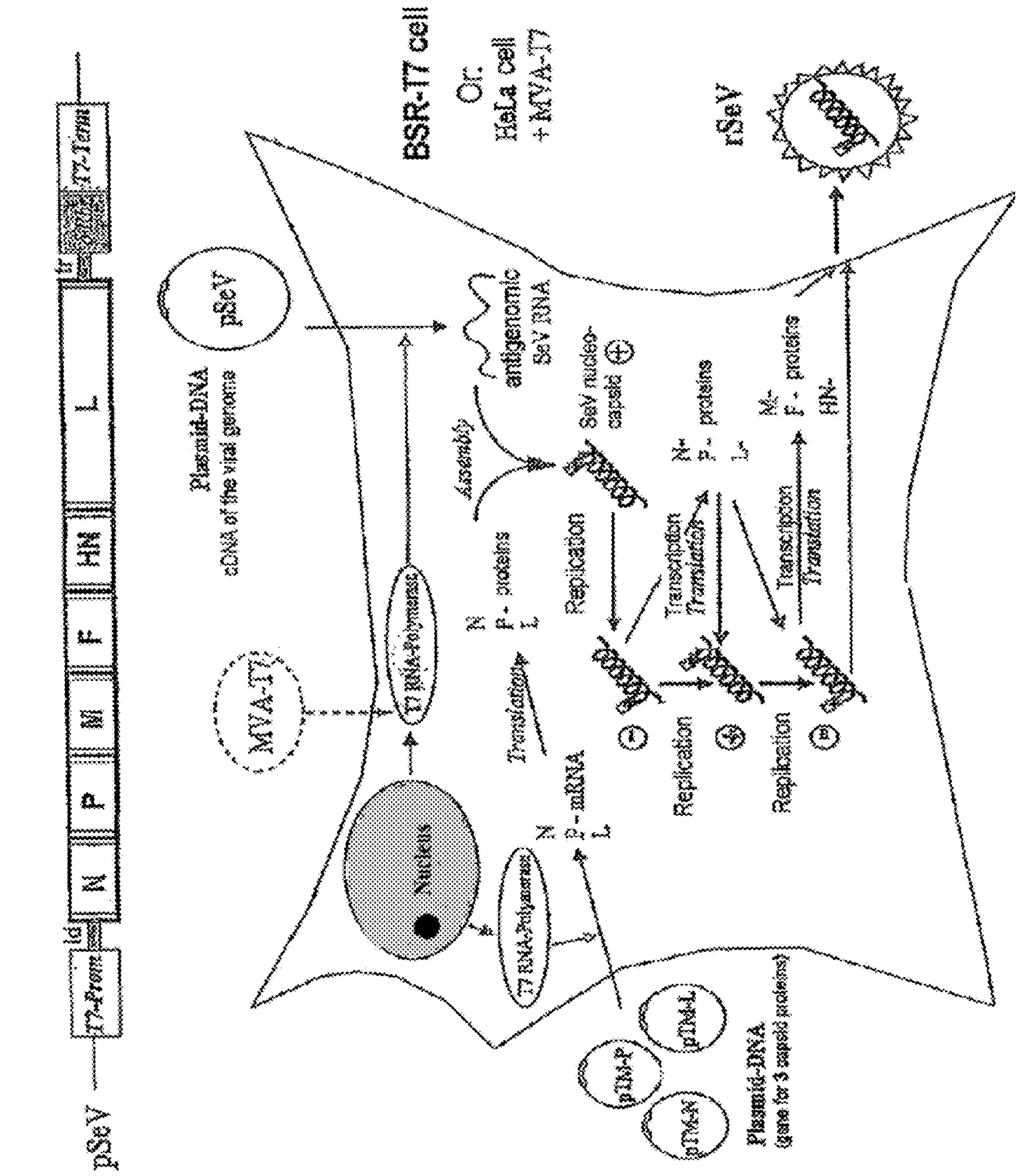
FIG. 10 illustrates the production of reactive SeV with a complete genome.

For the production of reactive SeV with a complete genome:

either the cell line "BSR-T7", which stably expresses the T7 RNA polymerase (Buchholz et al. (1999) J. Virol. 73, 251-259)

or cell cultures are infected with the recombinant vaccinia virus MVA-T7, which expresses T7 RNA polymerase (Sutter et al. (1995) FEBS 371, 9-12), and transfected with the cDNA of the viral genome (pSeV) and the plasmid-encoded genes N, P and L (pTM-N, -P, -L; Elroy-Stein et al. (1989) PNAS 86, 6126-6130). The T7 polymerase now transcribes the viral antigenome and/or the complementary sequence and the genes N, P and L. The N protein expressed via pTM-N packages the synthesized viral antigenomic and/or complementary RNA, and this nucleocapsid core (RNP) forms, together with the proteins P and L, the replication complex, via which genomic RNA can in turn be produced and packaged as nucleocapsids (Leyrer et al., J. Virol. Meth. 75 (1998), 47-55). This is followed by transcription of all virus-encoded proteins and replication of further viral genomes (FIG. 10).

In contrast to the production of recombinant SeV wt with complete genome described, the plasmid-encoded cDNA of pSeVV-eGFP-ΔN, -ΔP and -ΔL lacks the genomic information of one of the genes N, P or L in each case. Accordingly the nucleocapsids initially produced are only able to express two of the genes N, P or L in each case. The amount of the missing protein required for multiplication of SeVV-eGFP-ΔN, -ΔP and -ΔL nucleocapsids must therefore be provided exclusively via the T7-promoter-controlled expression of the plasmid-encoded genes N, P and L. Production of the replication-deficient SeVV-eGFP-AN, -AP and -ΔL was similar to the production of replication-competent SeV variants in HeLa cells (ATCC CCL2) or BSR-T7 cells. After incubation of the HeLa cells for 48 hours, we investigated whether viral particles of SeVV-eGFP-ΔN, -ΔP or -ΔL had been released into the culture supernatants, and how many initial deletion mutants had been produced.

4.2. Detection of initially produced SeVV-eGFP-ΔN, -ΔP or -ΔL

The supernatants of HeLa cells or BSR-T7 cells, in which SeVV-eGFP-ΔN, -ΔP or -ΔL should have been produced initially, were investigated for the presence of these viral vectors. SeVV-eGFP-ΔN, -ΔP or -ΔL have, in contrast to the recombinant SeV wt, the reporter gene for eGFP integrated in the 3' region. This detection marker was now used for analyzing how many SeVV-eGFP-ΔX had been formed.

In parallel assays, $5\times10^5$ Vero cells (ATCC CCL18) were in each case co-infected with 1 ml of cell culture supernatant of the HeLa cells transfected during the initial production of SeVV-eGFP-ΔN, -ΔP and -ΔL, and simultaneously with SeV wt (MOI=3) for transcomplementation of the missing protein. As control, Vero cells were infected either only with 1 ml of the initially produced SeV-eGFP or alternatively with initially produced SeV-eGFP and simultaneously with SeV wt (MOI=3).

The result of co-infection of cells with culture supernatants from production of SeVV-eGFP-ΔN, -ΔP or -ΔL, and SeV wt shows that all three virus mutants SeVV-eGFP-AX can be produced initially and after initial production are also capable of infecting cells, which can be detected by a detectable eGFP transgene expression. Approximately $13\times10^2$ SeV-eGFP, $6.7\times10^2$ SeVV-eGFP-ΔN, $3.2\times10^2$ SeVV-eGFP-ΔP and $0.55\times10^2$ SeVV-eGFP-ΔL virus mutants can be produced initially.

5. Multiplication of SeW-eGFP-Δ

Investigations were conducted to determine whether SeVV-eGFP-ΔX vecotrs are multipliable, i.e. are biologically functional. Capacity for replication was first to be investigated by preparing the proteins of the missing genes N, P or L by viral transcomplementation with SeV.

5.1 Demonstration of the Ability of SeVV-eGFP-ΔX to Multiply

It was first necessary to demonstrate that the mutants, on corresponding transcomplementation by the SeV wt virus, are able to multiply and infect the surrounding cells. For investigating the ability of SeVV-eGFP-ΔX to multiply, it is again possible to use co-infection of cells with SeVV-eGFP-ΔX and SeV wt. In this test the cells were infected with SeV wt at low MOI, co-infected with SeVV-eGFP-ΔX and incubated for several days, so as to be able to detect the spread of the SeVV-eGFP-ΔX vectors from the increasing number of fluorescing cells.

$5\times10^5$ Vero cells were infected simultaneously with on average 100 initially produced SeVV-eGFP-ΔN, ΔP or -ΔL and SeV wt (MOI=0.2). Co-infection of Vero cells with about 100 particles of the replication-competent virus SeV-eGFP and SeV wt was used as positive control. During a 48-hour incubation phase, multiplication of all three deletion mutants was observed: in each case, at first there was only fluorescence of individual Vero cells, which had been co-infected with SeVV-eGFP-ΔX and SeV wt. After about 24 h, newly synthesized virus particles were released from these cells, and were capable of penetrating nearby cells. If these cells were also infected simultaneously with SeVV-eGFP-ΔX and SeV wt, there was also detectable fluorescence in those cells. The multiplication of SeVV-eGFP-ΔN, -ΔP and -ΔL in cells co-infected with wt could be detected from this “tailing” of fluorescing cells 48 h p.i. and beyond.

This test established that the genomic cDNA constructs, from which SeVV-eGFP-ΔN, -ΔP and -ΔL were derived, are functional in all regions. It could also be shown that multiplication of virus mutants is possible on adding the missing viral protein. The protein (e.g. P) produced exclusively by wt virus is sufficient for multiplying both the deletion mutant and the wt, i.e. even a possibly suboptimal amount of P protein leads to the formation of functional nucleocapsids of SeV wt and SeVV-eGFP-ΔP. Supply of the missing protein by the transcomplementation partner SeV wt led to visible multiplication of all SeVV-eGFP-ΔX, measured from the increase in fluorescing cells in the cultures.

5.2 Determination of the Proteins Required for Multiplication of SeW-eGFP-ΔX

Next we investigated which proteins must be made available by a helper cell in each individual case of multiplication of SeVV-eGFP-ΔN, -ΔP and -ΔL, if it is to be possible for the SeV proteins N, P and L to be synthesized independently of one another. The three recombinant vaccinia viruses (VV) VV-N, VV-P and VV-L, which provide recombinant expression of the SeV proteins N, P or L, were available for independent synthesis of the SeV proteins N, P and L (Graef, H. (1994) Functional characterization of the recombinant Sendai virus large (L) protein. Thesis, Eberhard-Karls University Tubingen).

$1\times10^6$ Vero cells were co-infected simultaneously with SeVV-eGFP-ΔX or SeV-eGFP (MOI=0.01) and VV. VV-N, -P and -L were used individually or in combinations (MOI=0.5). After an adsorption time of one hour, the medium was replaced with DMEM+10% fetal calf serum (FCS)+cytosine-arabinoside (AraC)(100 pg/ml) and the cells were incubated for 72 h at 33° C., changing the medium daily, to add fresh AraC.

The propagation of SeVV-eGFP-ΔX was analyzed via eGFP expression after 72 h. In this time, in the positive assays there was multiplication of green-fluorescing cells from one initial cell to 10-30 adjacent fluorescing cells.

The results of the investigation of which SeV proteins are necessary for the multiplication of SeVV-eGFP-ΔN, -ΔP or -ΔL in Vero cells are presented in Table 2. Just expression of SeV N by VV-N does not lead to multiplication of SeVV-eGFP-ΔN. SeVV-eGFP-ΔN only multiplies if the SeV proteins N and P are expressed simultaneously in the infected cell by means of recombinant vaccinia viruses VV-N and VV-P. SeVV-eGFP-ΔP can be multiplied just by the expression of SeV P proteins by means of VV-P in Vero cells. Multiplication of SeVV-eGFP-ΔL required simultaneous synthesis of proteins P and L by VV. No multiplication of SeVV-eGFP-LL occurs in an SeVV-eGFP-ΔL and only VV-L infected Vero cell.

TABLE 2

SeV proteins required for multiplication of SeVV-eGFP-ΔX

| | | in vitro multiplication by means of VV |
|---|---|---|
| SeVV-eGFP-ΔN | N− | (N + P)+ |
| SeW-eGFP-ΔP | P+ | (N + P)+ |
| SeW-eGFP-ΔL | L− | (L + P)+ |

For the multiplication of SeVV-eGFP-ΔN, a helper cell must express the SeV proteins N and P simultaneously, expression of SeV P protein in the helper cell is sufficient for multiplication of SeVV-eGFP-ΔP, and the amplification of SeVV-eGFP-ΔL should be possible by cellular expression of the SeV proteins P and L.

5.3 Supporting of Amplification of SeVV-eGFP-ΔX by 1129 Helper Cells

For the investigations of the multiplication of SeVV-eGFP-ΔX with the aid of the H29 cell line, $1\times10^6$ H29 cells in four different assays were each infected with approx. 100 SeVV-eGFP-ΔN, -ΔP and -ΔL virus particles initially produced in HeLa cells or, as control for the successful multiplication of replicable SeV in H29 cells, with about 100 SeV-eGFP virus particles. In the period from 1 to 10 d p.i., investigation of the multiplication of SeVV-eGFP-ΔX was based on detection of a tail-like spread of the fluorescing cells (spot formation), starting from an initially infected H29 cell.

Multiplication of SeV-eGFP was observed in the control assay, starting from singly fluorescing cells 1 d p.i. to spots with up to 50 fluorescing cells 3 d p.i. It was thus established that the selected test setup leads to multiplication of SeV.

Virus multiplication also occurred in H29 cells infected with SeVV-eGFP-ΔN. In addition to H29 (a derivative of human 293 renal cells), derivatives of Vero cells (renal cells of the African green monkey) and derivatives of LLCMK2 cells (renal cells of the rhesus monkey), stably transfected with SeV P and N genes, are also suitable for virus multiplication.

In the assay with SeVV-eGFP-ΔP, about a hundred initially infected individual cells could be detected 1 d p.i. About 70% of the fluorescing individual cells had developed to spots, with up to 30 fluorescing cells, 3 d p.i. Therefore propagation of SeVV-eGFP-ΔP to surrounding H29 cells could definitely be observed. Thus, it is possible for the first time to multiply a viral SeV vector whose P-ORF has been deleted. Characterization of the multiplication of SeVV-eGFP-ΔP will be discussed in the next subsection.

5.4 Multiplication of SeVV-eGFP-ΔP on 1129 Cells

SeVV-eGFP-ΔP can be amplified by the SeV P proteins produced by H29 helper cells. The P-deletion mutants released are able to infect surrounding H29 cells. It was now necessary to analyze the propagation of SeVV-eGFP-ΔP in comparison with the propagation of the replication-competent SeV-eGFP.

For this purpose, $1\times10^6$ H29 cells were infected with on average 100 SeVV-eGFP-ΔP or SeV-eGFP. 3, 5 and 10 days p.i., green-fluorescing cells were detected using the fluorescence microscope.

SeVV-eGFP-ΔP could be multiplied successfully by cellular supply of SeV P proteins. It was found, at all times of investigation, that SeVV-eGFP-ΔP and SeV-eGFP multiply efficiently on H29 cells. In contrast, propagation of SeVV-eGFP-LP to cells that do not supply the missing P protein ("target cells", e.g. Vero cells) was not observed, which confirms that SeVV-eGFP-ΔP is replication-deficient (see Section 8).

5.5 Gene Expression of SeVV-eGFP-ΔP in Infected Target Cells

Absence of multiplication of SeVV-eGFP-ΔP on cell types which do not supply the P protein in trans was verified. At the same time, capacity for expression was way below expectations.

As in the case of the rabies virus np mutant (Shoji et al. (2004) Virology 318, 295-305), very few infected cells displayed a weak eGFP fluorescence (less than 5%; see FIG. 11), although statistically at an MOI=1 in fact approx. 70% of the cells are each infected with one virus particle. Even at a higher MOI=5, only isolated green-fluorescing Vero cells are observed due to SeVV-eGFP-ΔP (see FIG. 12, top left).

This confirms the assumption that after a cell is infected with a P gene-deficient virus, only a primary transcription is possible via the polymerase complex that is also supplied from the virus particle. In the case of the SeV ΔP mutant, furthermore, apparently only a small percentage of the infecting particles are capable of that, or gene expression is only observed if several transcribable nucleocapsids are present simultaneously in a cell.

For a therapeutic application of this replication-deficient SeVV, the capacity for expression seems too weak, or disproportionately many particles of SeVV ΔP would have to be applied per patient. Therefore it is desirable to use a replication-deficient SeV variant that also performs a secondary transcription. This leads to the development of additional modified polymerase complexes, which cannot replicate the viral genome, but are capable of increased expression of the therapeutic gene or antigen.

6. Production of a Modified SeVV-eGFP-ΔP cDNA Construct

For possible improvement of the transcription capacity of P gene-deficient SeVV in the target cell, another recombinant construct was produced, which codes for a form of the P protein shortened by 76 amino acids at the N-terminal end, at the position of the original P reading frame ("pSeVV-eGFP-PΔ2-77"; see Section 3.1 and FIG. 8B).

SeVV-eGFP-PΔ2-77 particles were generated and multiplied as in Section 4.1 and 5.4.

6.1 Growth Behavior of Seal-eGFP-PΔ2-77 in 1129 Helper Cells

In SeVV-eGFP-PΔ2-77 infected H29 helper cells, the viral-encoded PΔ2-77 protein, shortened by 76 amino acids at the N-terminal end, is synthesized together with the cellular-encoded P protein.

In order to investgate the effect of expression of the shortened P protein PΔ77 on viral replication, H29 cells were infected (MOI=3) with SeVV-eGFP-PΔ2-77, SeVV-eGFP-ΔP or the control virus SeV-eGFP as in the method described with reference to the growth kinetics of SeV-eGFP-ΔP. the Supernatants of the individual assays were determined over a period of 120 h by a cell infection dose test of the titers of progeny viruses from the number of eGFP-expressing cells.

From one SeV-eGFP infected H29 cell (positive control), on average 80 virus particles are released in a period of 120 h, and in this case transcomplementation of the P protein by H29 cells was not required. In the H29 transcomplementation system, SeVV-eGFP-PΔ2-77 could be multiplied with about equal efficiancey as SeVV-eGFP-ΔP: From infected H29 cells, after 120 h about $20\times10^6$ virus particles of SeVV-eGFP-ΔP or SeVV-eGFP-PΔ2-77 are released, which corresponds to a number of about 40 released virus particles of the P mutants per H29 cell.

7. Comparison of Gene Expression of SeVV-eGFP-ΔP and SeVV-eGFP-PΔ2-77 and Quantification of Protein Synthesis in Infected Target Cells To investigate whether the vector SeVV-eGFP-PΔ2-77 displays increased transgene expression—compared with SeVV-eGFP-ΔP—in infected target cells, the virus-encoded expression of the reporter gene eGFP and of the HN protein was characterized in detail.

$5\times10^5$ Vero cells were infected with SeVV-eGFP-PΔ2-77 (MOT=1), and on day 2 p.i. approx. 70% fluorescing Vero cells were observed (not shown). This means that almost every RNP complex of this viral vector variant is capable of inducing a measurable transcription in the target cell 7.1 Quantification of eGFP Expression by FACS Analysis In subsequent applications in the medical area, the transcription cassette, into which the reporter gene eGFP in SeVV-eGFP-PΔ2-77 was inserted, is to encode the antigen of a pathogen, e.g. of a desired virus. This antigen expression must be sufficient to elicit a protective immune response in the patient.

In order to establish that each SeVV-eGFP-PΔ2-77 nucleocapsid that infects a target cell is able to perform a detectable transgene expression, the same number of H29 and Vero cells were infected with the same quantity of virus particles and the number of eGFP-expressing H29 or Vero cells were compared by FACS (fluorescence-activated cell sorting) analysis using a FACS-Calibur flow cytometer. The data were evaluated from a computer-generated histogram, plotting the fluorescence signals of infected cells against the total cell count.

Figure 11:
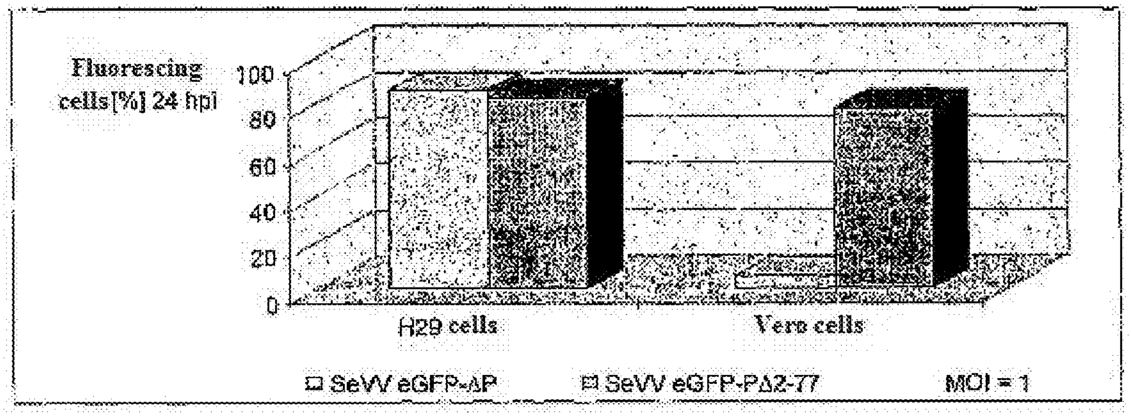
FIG. 11 is a bar graph showing fluorescing cells determined by flow cytometry.

$2.5\times10^5$ Vero cells or H29 cells were infected with SeVV-eGFP-PΔ2-77 or with the P gene-deficient virus SeVV-eGFP-ΔP at MOI=1. FACS analysis of the samples was carried out 24 h after infection. The infected cells were taken up in PBS and the number of fluorescing cells was determined by flow cytometry. The result is shown in FIG. 11 as the proportion [%] of fluorescing Vero and H29 cells.

24 h after infection of H29 helper cells with SeVV-eGFP-ΔP, 86% eGFP-expressing H29 cells were detected by FACS analysis. Cellular synthesis of the P protein supports the formation of new P:L complexes and therefore production of new mRNA, which leads to synthesis of eGFP proteins in the infected cell. However, when Vero cells were infected with SeVV-eGFP-ΔP, expression of the eGFP protein was not detected 24 h p.i. nor at a later time in additional assays. The P:L complexes transferred by SeVV-eGFP-ΔP nucleocapsids are not able, on infection at MOI=1, to bring about detectable expression in infected Vero cells.

In contrast, 24 h after SeVV-eGFP-PΔ2-77 infection, almost 80% eGFP-expressing H29 cells and likewise 75% eGFP-expressing Vero cells were identified by FACS analysis. When H29 cells are infected, transcription of the eGFP mRNA can be supported by the cellular synthesis of the P protein and therefore by new P:L complexes. When Vero cells are infected with SeVV-eGFP-PΔ2-77, transcription is intensified by new synthesis of the P protein PΔ2-77 shortened at the N-terminal end.

Based on these results, an important statement can be made concerning the number of transcribable SeVV-eGFP-PΔ2-77: H29 cells and Vero cells were infected with an MOI of 1. Theoretically occurring multiple infections of a cell are statistically of equally low probability in both assays. 24 h p.i., almost 80% of eGFP-expressing H29 cells and about 75% eGFP-expressing Vero cells were identified. It can therefore be concluded that each RNP complex with the shortened P-variant PΔ2-77, which is capable of transgene expression in a P helper cell, likewise brings about transgene expression in the infected target cell. In contrast, the variant SeVV-eGFP-ΔP with a complete deletion of the P ORF does not have this property.

7.2 Function Test of the HN Protein Expressed in Infected Target Cells

Figure 12:
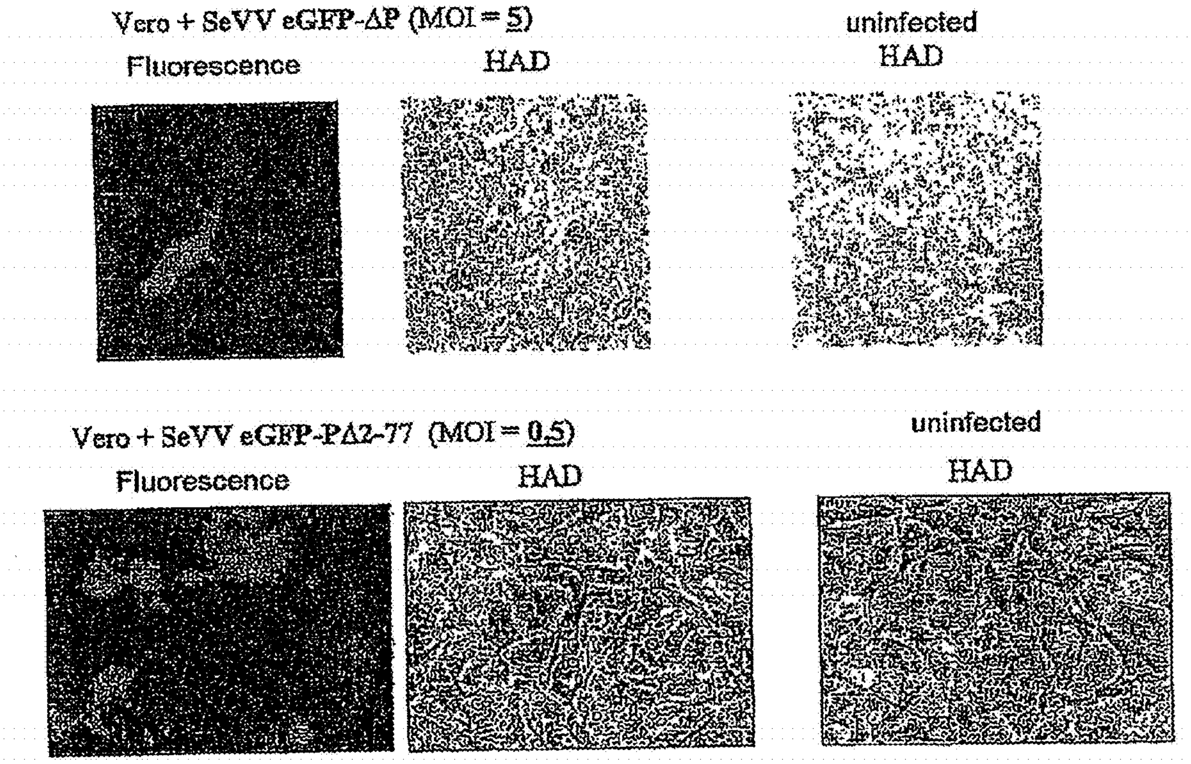
FIG. 12 shows fluorescing cells as observed under microscope.

The efficiency of binding of human erythrocytes and therefore the efficiency of exposure of viral HN proteins on individual infected cells were detected using a heme adsorption (HAD) test (FIG. 12).

$5\times10^5$ Vero cells were infected with SeVV-eGFP-PΔ2-77 at a low MOI=0.5. In contrast, in the case of SeVV-eGFP-ΔP, Vero cells had to be infected with a 10-times higher MOI=5, to be able to observe even occasional fluorescing cells. After 1 h adsorption, the medium was replaced with DMEM+10% FCS. Then the cells were incubated at 33° C. for several days. At first, the transgene expression of both vector variants was monitored from the eGFP fluorescence. On day 5 and 9 p.i., HAD test series were performed, for analyzing the exposure of the viral HN proteins on the basis of binding of human erythrocytes.

Although in the case of SeVV-eGFP-ΔP, at MOI=5, statistically 99.3% of the Vero cells ought to be infected, only 0.01% eGFP-positive cells could be observed under the microscope (FIG. 12 top left). In contrast, with SeVV-eGFP-PΔ2-77 a green fluorescence is seen at MOI=0.5 in 40% of the cells, as was expected (FIG. 12 bottom left).

Two days after infection with SeVV-eGFP-ΔP, only half of the eGFP-positive cells (25 of $5\times10^5$ infected) were capable of binding erythrocytes on their surface (FIG. 12 top centre). After further incubation and HAD testing again, there was no longer adsorption of erythrocytes on infected cells. With the second replication-deficient SeVV variant SeVV-eGFP-PΔ2-77, much better results were achieved: 5 days after infection, approx. 40% of the infected cells (MOI=0.5) were capable of binding erythrocytes on their surface (FIG. 12 bottom center). A variation in binding activity from 10 to 70 complexed red blood cells was observed for the individual cells. It had thus been shown that cells infected with SeVV-eGFP-PΔ2-77 are capable, 5 d p.i., of exposing HN proteins on the cell surface, and the functional HAD test can be assessed as positive. At the same time, efficient expression of the HN protein in the infected cells was found, based on the difference in quantity of bound erythrocytes.

The infected cells were further incubated at 33° C., during which the neuraminidase activity of the HN protein causes the erythrocytes bound to infected cells to be released. The cells were washed to remove the released erythrocytes, and incubated for a further 4 d at 33° C. A HAD test was performed again on day 9 p.i. About 30% HAD-positive Vero cells were now detected. The number of bound red blood cells dropped to 5-20 erythrocytes per cell.

Thus, 9 days i.p., sufficient functional HN was still synthesized by the replication-deficient variant SeVV-eGFP-PL\2-77. In contrast, the variant SeVV-eGFP-ΔP with complete deletion of the P ORF does not have these properties.

7.3 Quantification of eGFP Expression by Western Blot Analysis

A semi-quantitative assessment of eGFP expression of the replication-deficient SeV vector in comparison with replication-competent SeV-eGFP was carried out by Western blot analysis using serial dilution of total cellular protein.

Figure 13:
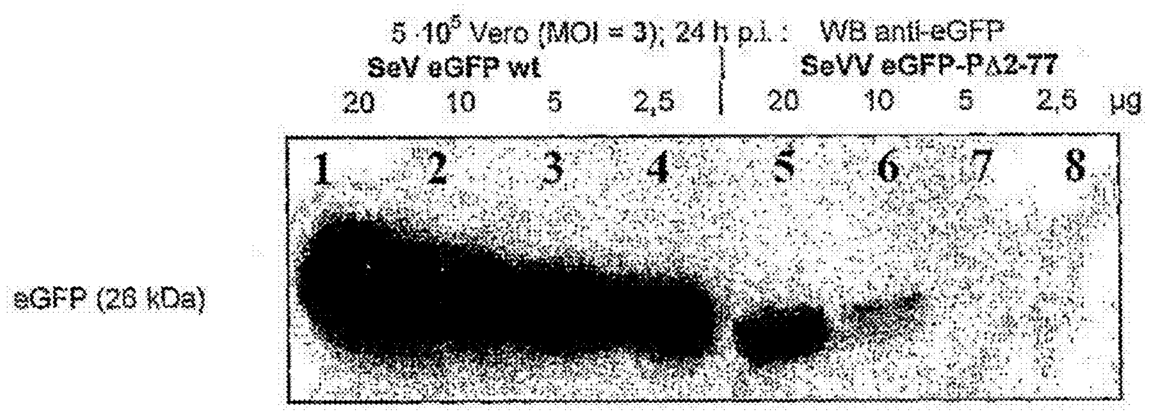
FIG. 13 shows western blot analysis of viral-encoded eGFP proteins.

$5\times10^5$ Vero cells were infected with SeV-eGFP or SeVV-eGFP-PΔ2-77 (MOI=3). Cell disruption was performed 24 h p.i. The cellular extracts were separated in SDS-PAGE in serial dilutions (1:2) from 20 pg to 2.5 pg total quantity. The proteins were transferred to a PVDF membrane and the viral-encoded eGFP protein (26 kDa) was detected first by Western blot analysis (FIG. 13).

The fluorescence protein eGFP was detected using Western blot analysis both in SeV-eGFP and in SeVV-eGFP-PΔ2-77 infected Vero cells. It can be concluded, from comparison of the intensities of the eGFP signals, that expression—mediated by the replication-deficient SeVV-eGFP-PΔ2-77—is reduced by about a factor of 16 compared with the replication-competent SeV-eGFP.

A reduction by a factor of 16 is slight, and it can therefore be concluded that despite the modified P protein, SeVV-eGFP-PΔ2-77 can produce very efficient secondary transcription.

7.4 Estimation of HN Expression by Western Blot Analysis

In contrast to the eGFP protein, the SeV HN protein is a membrane-bound surface protein and is an important antigenic determinant. By relative quantification of the level of expression of the HN protein in SeVV-eGFP-PΔ2-77 infected cells, a conclusion could be drawn concerning the intensity of expression of the SeV HN antigen.

Figure 14:
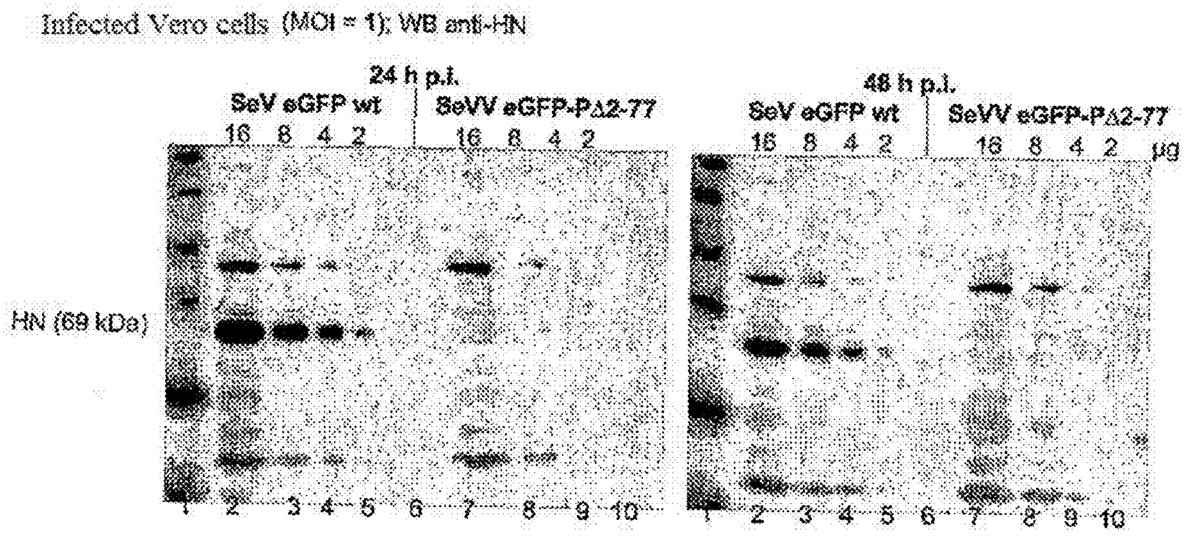
FIG. 14 shows the result of monoclonal HN-antibody detection of viral-encoded HN protein.

A semi-quantitative assessment of HN expression of the replication-deficient SeV vector in comparison with the replication-competent SeV-eGFP was carried out by Western blot analysis using serial dilutions of total cellular protein. In each case, $5\times10^5$ Vero cells were infected with SeV-eGFP or SeVV-eGFP-PΔ2-77 in 2 parallel assays (MOI=1) and incubated for 24 h or 48 h. Then the cells were disrupted. The cellular extracts were separated in SDS-PAGE in serial dilutions (1:2) from 16 μg to 2 μg total quantity. The proteins were transferred to a PVDF membrane and the viral-encoded HN protein (60 kDa) was detected by means of a monoclonal HN-antibody (FIG. 14).

The HN protein was detected efficiently in the case of SeV-eGFP infected Vero cells after both incubation times in all traces (16 to 2 μg total protein; traces 2-5 left and right). In the case of SeVV-eGFP-PΔ2-77, the band of the HN protein is still visible in the traces with 16 and 8 μg total protein (trace 7, 8), though at lower intensity. Relative quantification of HN expression in SeVV-eGFP-PΔ2-77 infected Vero cells relative to SeV-eGFP was carried out by comparing the traces with 16 and 8 μg vs. 2 μg total protein (traces 7 and 8 vs. 5, left and right) and permits an estimated reduction of HN expression by a factor of 8-16 of the P-deletion variant, regardless of the incubation time. It can be concluded that the transcription rate in SeVV-eGFP-PΔ2-77 infected cells is relatively high, and therefore transgene expression of the viral replication-deficient vector is generally high.

Taking both measurements (eGFP protein and HN protein) into account, it can be assumed that there is an average reduction of expression by a factor of 10.

8. Replication Deficiency of SeVV-eGFP-PΔ2-77 in the Target Cell

If Vero cells are infected with the replication-competent SeV-eGFP, in the next two days a spot comprising up to a thousand additional fluorescing cells forms around the initially infected, strongly fluorescing cell. To prove the replication deficiency of SeVV-eGFP-PΔ2-77 in Vero cells, it was necessary to confirm the absence of this increase in green-fluorescing cells around the initially infected target cell, taking into account the natural rate of division of Vero cells. Vero cells divide on average every 24 h. If Vero cells are infected with SeVV-eGFP-PΔ2-77, a detectable eGFP expression can be seen after about 24 h. It was observed that after a further 24 h incubation phase, in some cases two (more weakly) fluorescing daughter cells are produced from this initially infected, fluorescing Vero cell on account of natural division. This observation has nothing to do with virus multiplication, in which between $10^1$ to $10^4$ virus particles are released from an infected target cell, and can then infect nearby cells. This natural rate of division of infected cells does not, however, affect the level of eGFP expression, which is reduced with increasing number of cell divisions. This observation shows that the viral vector SeVV-eGFP-PΔ2-77 is genome-replication-deficient, so no new genomes are synthesized. If several successive cell divisions of an infected cell lead to a continuous decrease in fluorescence intensity, until it finally stops, virus multiplication can be ruled out.

For final confirmation of the replication deficiency of SeVV-eGFP-PΔ2-77 in target cells, one last study was conducted:

$20\times10^6$ Vero cells were placed in a T75 flask. The cells had been seeded at high density at the beginning of the incubation phase and accordingly were no longer dividing actively. These Vero cells were infected with SeVV-eGFP-PΔ2-77 at an MOI of 0.001. The medium was changed to DMEM with 5% FCS (for reduced activity of division) after incubation for 1 hour, and the Vero cells were incubated at 33° C. (P1). Two days p.i., according to the selected MOI, initially several thousand separate infected, fluorescing Vero cells were observed. Owing to the high cell density, over the next 4 days of incubation there was hardly any cell division, i.e. the number of initially infected cells, detected by fluorescence, remained constant. If virus particles had been formed in this period, they would have been able to infect nearby cells, and this would have been reflected in increased fluorescence. Even after 8 days, propagation of the viral vector could be ruled out, owing to absence of new infections of surrounding cells. To supply the cells with fresh medium, the supernatant was removed and the Vero cells were covered with fresh medium. 12 days after the start of incubation, the Vero cells became detached from the culture medium. For the whole test period, no replication of the viral vector was observed in the form of an increase in fluorescing cells. Propagation of SeVV-eGFP-PΔ2-77 from the originally infected cells to surrounding Vero cells by production of new virus genomes and particles could thus be ruled out. Therefore SeVV-eGFP-PΔ2-77 can be described as a replication-deficient viral vector.

Summary

The above results show that specific manipulations of genes for components of the polymerase complex can lead to the production of replication-deficient negative-strand RNA viruses, which are still able to transcribe the virus-encoded genes, but are no longer able to replicate the viral genome.

In the case of the Sendai virus, two particular variants were investigated more closely, in which the gene for the polymerase cofactor phosphoprotein was deleted completely ("SeVV-eGFP-ΔP") or the codons for amino acids 2 to 77 were removed ("SeVV-eGFP-PΔ2-77"). Both SeV vectors are replication-deficient in cells which do not supply the P protein in trans (so-called target cells), but they differ considerably in their capacity for gene expression.

Although in the case of SeVV-eGFP-ΔP at an MOI=5, statistically only 0.7% of the Vero cells remain uninfected—99.3% should contain at least one RNP complex—only 0.01% eGFP-positive cells were observed under the microscope. It can be concluded from this mathematically that visible transgene expression only occurs if 15 or more RNPs of SeVV-eGFP-ΔP are present simultaneously in an infected target cell.

This P gene-deficient SeVV displays similar weak expression as the analogous rabies ΔP variant (Shoji et al., supra). Both vectors are only capable of primary transcription in the infected target cell, via the polymerase complex that is supplied from the virus particle. However, stronger expression of the encoded transgene or antigen is desired for therapeutic application of the vector. This condition can be fulfilled with the aid of the replication-deficient variant SeVV-eGFP-PΔ2-77, which only gives a capacity for expression in the target cells that is reduced on average by a factor of 10 in comparison with replication-competent SeV. Owing to the presence of the gene for a P protein shortened at the N-terminal end in the vector genome, not only primary, but also secondary transcription is possible. This is realized with newly formed, modified polymerase complexes, which contain the vector-encoded PΔ2-77 protein; this does not, however, support the replication mode of polymerase. Quantification of protein synthesis in infected target cells has demonstrated that the replication-deficient viral vector SeVV-eGFP-PΔ2-77 is capable of performing efficient transcription and expression of viral-encoded genes. Not only is the 3'-proximal transgene (eGFP) effectively synthesized; the HN gene located at genome position 6 is transcribed for at least 9 days after infection and the protein is exposed functionally on infected target cells.

9. Determination of the Immune Response Induced in a Mouse Model by a Replication-Deficient RNA Vaccine It was shown that preferably by a deletion in the P gene ("PΔ2-77") an altered viral polymerase complex is produced, which no longer allows synthesis of new genomes. At the same time, after infection with these replication-deficient viruses, the viral gene expression mediated in the target cell is only approx. 10× lower in comparison with infections with replication-competent virus.

In order to demonstrate a sufficiently immunogenic property of the replication-deficient negative-strand RNA virus as vaccination vector, antigens or antigenic determinants of two heterologous viruses (human parainfluenza virus type 3, hPIV3, and respiratory syncytial virus, RSV) were inserted in the virus genome: for this, a replication-deficient SeV PΔ2-77 was constructed, in which the genes of the original surface proteins F and HN were replaced with genes coding for chimeric F and HN proteins SeV/hPIV3. The chimeric F protein contains 558 amino acids and comprises the extracellular domain of hPIV3 (493 amino acids), the transmembrane domain of SeV (23 amino acids) and the cytoplasmic domain of SeV (42 amino acids). The chimeric HN protein has 579 amino acids and comprises the cytoplasmic domain of SeV (35 amino acids), the transmembrane domain of SeV (25 amino acids) and the extracellular domain of hPIV3 (519 amino acids). The amino acid sequences of the chimeric F protein and of the chimeric HN protein are shown in the sequence listing as SEQ ID No. 27 and 28.

Inserting chimeric genes in the virus genome produces a novel antigenicity and in addition ensures efficient assembly of vaccine particles during their production.

The surface protein F of RSV was encoded in an additional expression cassette interposed between two viral genes, so that the construct was extended to a bivalent vaccine.

Figure 15A:
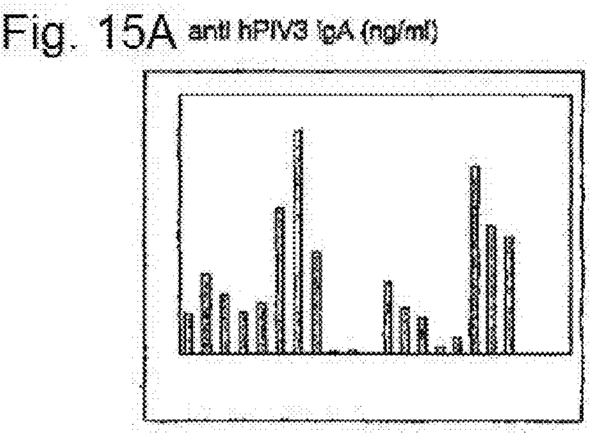
FIG. 15A shows the induction of IgA antibodies against hPIV3 by replication-deficient vaccine.
Figure 15B:
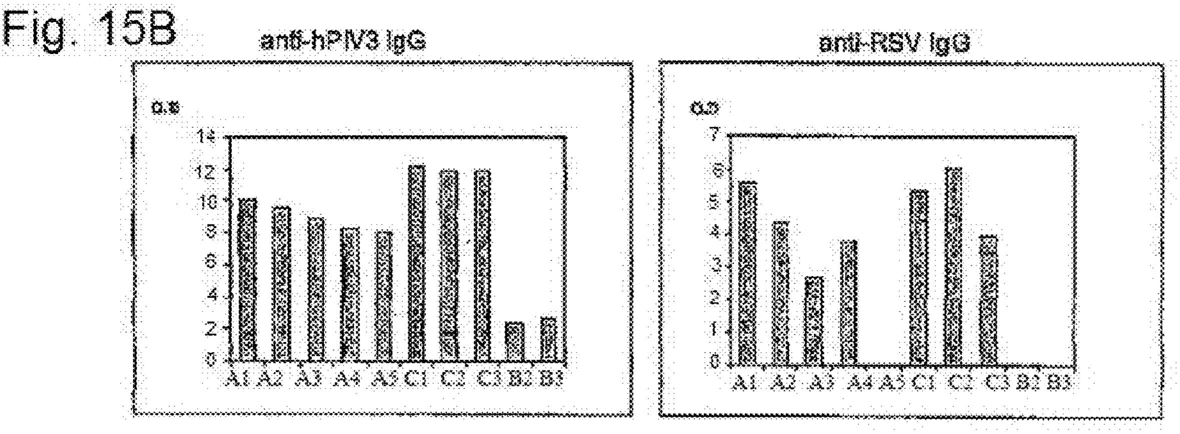
FIG. 15B shows the induction of a humoral immune response to the surface antigens of both viruses.

This new vaccine was tested in an animal model. Groups of Balb/C mice were immunized intranasally three times with two different virus preparations (group A or C, $10^4$ infectious units each) at intervals of three weeks, and a control group (B) received PBS instead of the vaccine. After the third immunization, nasal wash fluid (NW) was obtained for analysis of the mucosal immune response, and broncho-alveolar (BAL) flushing was carried out, and the serum was isolated for analysis of the humoral immune response. Using ELISA, we determined the quantity of induced immunoglobulins IgA and IgG specifically against hPIV3 and RSV. The replication-deficient vaccine prototype produced a definite induction of IgA antibodies specifically against hPIV3 (FIG. 15A), but there was less induction of anti-RSV IgA antibodies (not shown). The induction of a humoral immune response to the surface antigens of both viruses produced comparable titers, and the amount of specific IgG differs by a factor of 2 (FIG. 15B). Further analysis of the anti-hPIV3-IgG showed that the induced antibodies have neutralizing properties (titer 1/64). In contrast, as expected, no specific IgA or IgG induction was found in the control group.

The vaccine according to the invention was able to induce a specific mucosal and humoral immune response to heterologous viral antigens. Additional experiments showed that lymphocytes of immunized mice produced interferon-y, whereas IL-5 could not be detected. This finding indicates that the bivalent, replication-deficient RNA vaccine is able to trigger a T-cell immune response, which is a prerequisite for long-lasting immunity.

Summary

Following infection of experimental animals with a modified vector, in which coding sequences for antigens of two heterologous viruses were inserted, the induction of neutralizing antibodies was detected. This shows the potential of replication-deficient negative-strand RNA viruses for the development of novel vaccines.

10. List of DNA Oligonucleotides Used

The DNA oligonucleotides used in the above examples are shown below in Table 3.

TABLE 3

| SEQ ID No. | Designation | Length [nt] | Sequence 5'-3' | Tm [° C.] |
|---|---|---|---|---|
| 1 | X I = M13 | 19 | GGAAACAGCTATGACCATG | 54 |
| 2 | X I (+) | 59 | GGATCATTAGTACCTTGAAGCCTCGT AGATCGCGGC | 56 |
| 3 | X II | 57 | GGCTTCAAGGTACTAATGATCCGTAG TAAGAAAAAC | 64 |
| 4 | X II (+) = N-1029 (+) | 18 | GGTAGGTGTCTATGAGGC | 56 |
| 5 | XX | 44 | GGAAGGAAAAGCGGCCGCCGGCGGG ATCATACGAGG CTTCAAGG | 61 |
| 6 | XX (+) | 57 | CCTGTGTTTCTGCGGCCGCCGTTCGCG AGGCCGGCC | 61 |
| 7 | NotI eGFP | 44 | CGCGGGCCCGGGGCGGCCGCGTCGCC ACCATGGTGA GCAAGGGC | 60 |
| 8 | eGFP NotI (+) | 26 | GATGCATGCTCGAGCGGCCGCTTTAC | 58 |
| 9 | SgrAI eGFP | 36 | GGATTACTATCGCCGGCGGTCGCCAC | 61 |

TABLE 3-continued

| SEQ ID No. | Designation | Length [nt] | Sequence 5'-3' | Tm [° C.] |
|---|---|---|---|---|
| 10 | eGFP SgrAI (+) | 37 | CGCTAACTGTCGCCGGCGTTTACTTGTACAGC TCGT | 63 |
| 11 | Fsel DsRed | 36 | CGGATCAAGTGGCCGGCCGTCGCCAC | 59 |
| 12 | DsRed Fsel (+) | 42 | CGCGAATATCGGCCGGCCAAGTCTAC AGGAACAGGT GGTGGC | 63 |
| 13 | ΔN I = M13 | 19 | GGAAACAGCTATGACCATG | 54 |
| 14 | ΔN I (+) | 35 | CGGTGCGGGCCCGCACGTGAACTTTG | 50 |
| 15 | ΔN II | 28 | GTTCACGTGCGGGCCCGATCATACGA | 44 |
| 16 | ΔN II (+) = P-2892 (+) | 19 | CGCGTCTCGGGATGATTCG | 62 |
| 17 | ΔP I = N-578 | 17 | CCCTGACACACTCCTTC | 54 |
| 18 | ΔP I (+) | 31 | GCGCCGCTCGAGGCGGTAAGTGTAGC | 64 |
| 19 | ΔP II | 34 | CCTGCGCTCGAGCTCATCCCGGGTGA | 64 |
| 20 | ΔP II (+) | 34 | GGCGACGCGTCAGTCTCACAGCCTAA | 64 |
| 21 | XhoI PΔ2-77 | 47 | CCCCCTTTTTCTCGAGATGTCGACCCA AGATAATCG ATCAGGTGAGG | 84 |
| 22 | PΔ2-77 (+) XhoI | 46 | TTTTTCCCCCCTCGAGTTACTAGTTGG | 80 |
| 23 | ΔL I = F-4871 | 20 | AGCATATATCCAGAGGTCAC | 58 |
| 24 | ΔL I (+) | 38 | GGGACTAATTAGTCGGGCCCGACC | 58 |
| 25 | ΔL II | 31 | GCACTTGGGCCCGACTAATTAGTCCC | 60 |
| 26 | ΔL II (+) | 21 | CGAATGGCGCGCCTGATGCGG | 64 |

The invention claimed is:

1. A recombinant Sendai virus, containing a viral genome with a deletion of amino acids 2-77 of the protein encoded by gene P, which leads to loss of capacity for replication without loss of capacity for secondary transcription, and at least one sequence coding for a heterologous gene product, wherein the heterologous gene product is a viral antigen.

2. The Sendai virus as claimed in claim 1, characterized in that the viral genome codes for several heterologous antigens from the same or different viruses.

3. The Sendai virus as claimed in claim 1, characterized in that the sequence coding for at least one heterologous gene product is inserted in the viral genome and/or replaces sequences coding for a homologous gene product.

4. The Sendai virus as claimed in claim 1, characterized in that the virus has a capacity for transcription that is reduced by at most a factor of 20 relative to the wild-type virus.

5. A nucleocapsid of the Sendai virus as claimed in claim 1.

6. A genome of the Sendai virus as claimed in claim 1.

7. A DNA molecule that codes for the genome and/or antigenome of the Sendai virus as claimed in claim 1.

8. The DNA molecule as claimed in claim 7, characterized in that it is linked operationally with a transcription signal.

9. The DNA molecule as claimed in claim 8, characterized in that the transcription signal is a bacteriophage promoter, preferably, a T7 or SP6 promoter.

10. A cell that contains the Sendai virus as claimed in claim 1, the nucleocapsid as claimed in claim 5, the genome as claimed in claim 6 or the DNA molecule as claimed in claim 7.

11. The cell as claimed in claim 10, characterized in that it is a vector multiplying cell.

12. The cell as claimed in claim 10, characterized in that it is a virus producing cell.

13. The cell as claimed in claim 10, characterized in that it further contains a DNA molecule coding for a heterologous DNA-dependent RNA polymerase, which effects the transcription of the DNA molecule coding for the recombinant Sendai virus.

14. The cell as claimed in claim 10, characterized in that it is a virus multiplying cell.

15. An in vitro method of production of the recombinant Sendai virus as claimed in claim 1, comprising the steps: (a) preparation of a cell that is transfected with a DNA molecule that codes for the genome of the recombinant Sendai virus, containing a mutation in gene P and said mutated gene P encodes for a P protein having deletion of amino acid 2-77 of the P protein, wherein said mutant P protein leads to loss of the capacity for viral genome replication without loss of the capacity for secondary transcription, and optionally at least one sequence coding for a heterologous gene product, and (b) cultivation of the cell under conditions such that a transcription of the DNA according to (a) takes place and the recombinant Sendai virus is formed.

16. The method as claimed in claim 15, further comprising the obtaining of the nucleocapsid or of the viral genome from the recombinant Sendai virus.

17. A pharmaceutical composition, characterized in that it contains the recombinant Sendai virus as claimed in claim 1, the nucleocapsid as claimed in claim 5 or the viral genome as claimed in claim 6 as active substance and optionally pharmaceutically acceptable vehicles and/or excipients.

18. The pharmaceutical composition as claimed in claim 17 as vaccine.

19. The pharmaceutical composition as claimed in claim 18 as a monovalent or polyvalent vaccine.

20. The pharmaceutical composition as claimed in claim 18 as a vaccine against viral infections, including as a vaccine against infections with pathogenic negative-strand RNA viruses.

21. The pharmaceutical composition as claimed in claim 17 as an antitumor agent.

22. The pharmaceutical composition as claimed in claim 17, comprising the nucleocapsid in the native viral envelope.

23. The Sendai virus as claimed in claim 1, characterized in that the viral antigen is an antigen of human parainfluenza virus type 3 (hPIV3) or respiratory syncytial virus (RSV).

24. The Sendai virus as claimed in claim 1, characterized in that the at least one sequence coding for a heterologous gene product is selected from SEQ ID No.27 and 28.

* * * * *